United States Patent [19]

Takase et al.

[11] Patent Number: 5,510,506

[45] Date of Patent: Apr. 23, 1996

[54] PROCESS FOR PRODUCING CARBOXYLIC ACID DERIVATIVES

[75] Inventors: Akira Takase, Otsu; Hiroyuki Kai, Yamatokoriyama; Moriyasu Masui, Yokkaichi; Katuhisa Masumoto, Ibaraki; Akihiko Nakamura, Takatsuki; Yujiro Kiyoshima, Oita; Mikio Sasaki, Ibaraki, all of Japan

[73] Assignees: Shionogi & Co., Ltd.; Sumitomo Chem.Co., Ltd., both of Osaka, Japan

[21] Appl. No.: 392,852

[22] PCT Filed: Jul. 1, 1994

[86] PCT No.: PCT/JP94/01075

§ 371 Date: Mar. 27, 1995

§ 102(e) Date: Mar. 27, 1995

[87] PCT Pub. No.: WO95/01328

PCT Pub. Date: Jan. 12, 1995

[30] Foreign Application Priority Data

| Jul. 2, 1993 | [JP] | Japan | 5-164710 |
| Jul. 2, 1993 | [JP] | Japan | 5-164711 |
| Jul. 2, 1993 | [JP] | Japan | 5-164712 |
| Feb. 17, 1994 | [JP] | Japan | 6-020497 |

[51] Int. Cl.$^6$ .................................................. C07C 229/02
[52] U.S. Cl. .................................................. 560/35
[58] Field of Search .................................................. 560/35

[56] References Cited

U.S. PATENT DOCUMENTS

| 4,233,233 | 11/1980 | Schroer . |
| 4,466,822 | 8/1984 | Martin . |
| 5,221,762 | 6/1993 | Wingert . |
| 5,354,883 | 10/1994 | Isak . |

FOREIGN PATENT DOCUMENTS

| 596692A2 | 11/1993 | European Pat. Off. . |
| 56-12360 | 6/1981 | Japan . |
| 4-288045 | 9/1991 | Japan . |
| 6-219986 | 8/1994 | Japan . |

*Primary Examiner*—José G. Dees
*Assistant Examiner*—Joseph M. Conrad III
*Attorney, Agent, or Firm*—Birch, Stewart, Kolasch & Birch

[57] ABSTRACT

A process is disclosed to produce a carboxylic acid derivative of the general formula [VIII]:

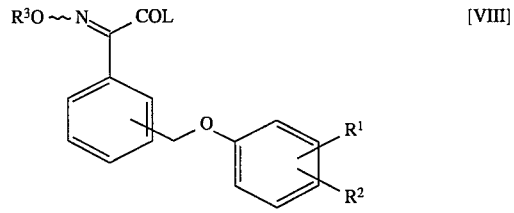

wherein $R^1$, $R^2$, $R^3$ and L are each as defined in the specification, characterized in that a benzyl halide is reacted with a cyano compound to give a phenylacetonitrile, which is then reacted with an alkyl nitrite in the presence of a base to give an α-hydroxyiminophenylacetonitrile, which is then reacted with an alkylating agent to give an α-alkoxyiminophenylacetonitrile, which is then hydrolyzed in the presence of a base, or is hydrated and treated with an acid, followed by hydrolysis in the presence of a base, to give an α-alkoxyiminophenylacetic acid, which is then reacted with an acid halide forming agent, or is convened into a metal salt, followed by reaction with an alkylating agent, or is reacted with a lower alcohol in the presence of an acid catalyst.

According to the present invention, the reactions can be allowed to proceed under mild conditions over the whole process, and the desired carboxylic acid derivative [VIII] can be produced without any facilities such as high-pressure steam equipment, high-temperature heat medium control equipment and freezing machines. In addition, there is no need to use various different solvents in the respective steps and the present process can be conducted with only one solvent, in which respect the present invention is also advantageous.

12 Claims, No Drawings

PROCESS FOR PRODUCING CARBOXYLIC ACID DERIVATIVES

This application is a 371 of PCT/JP94/01075.

TECHNICAL FIELD

The present invention relates to a process for producing carboxylic acid derivatives of the general formula [VIII]:

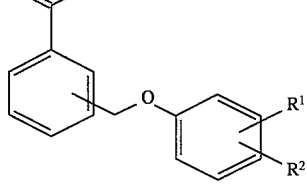

[VIII]

wherein $R^1$ and $R^2$ are the same or different and are independently hydrogen, $C_1$-$C_5$ alkyl, $C_1$-$C_5$ alkoxy, $C_2$-$C_4$ alkenyl, halogen or trifluoromethyl, $R^3$ is $C_1$-$C_5$ alkyl, and L is halogen or $C_1$-$C_5$ alkoxy.

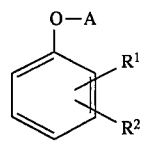

[I]

wherein $R^1$ and $R^2$ are each as defined above and A is an alkali metal or an alkaline earth metal, are used as the starting material (JP-A 4-295454):

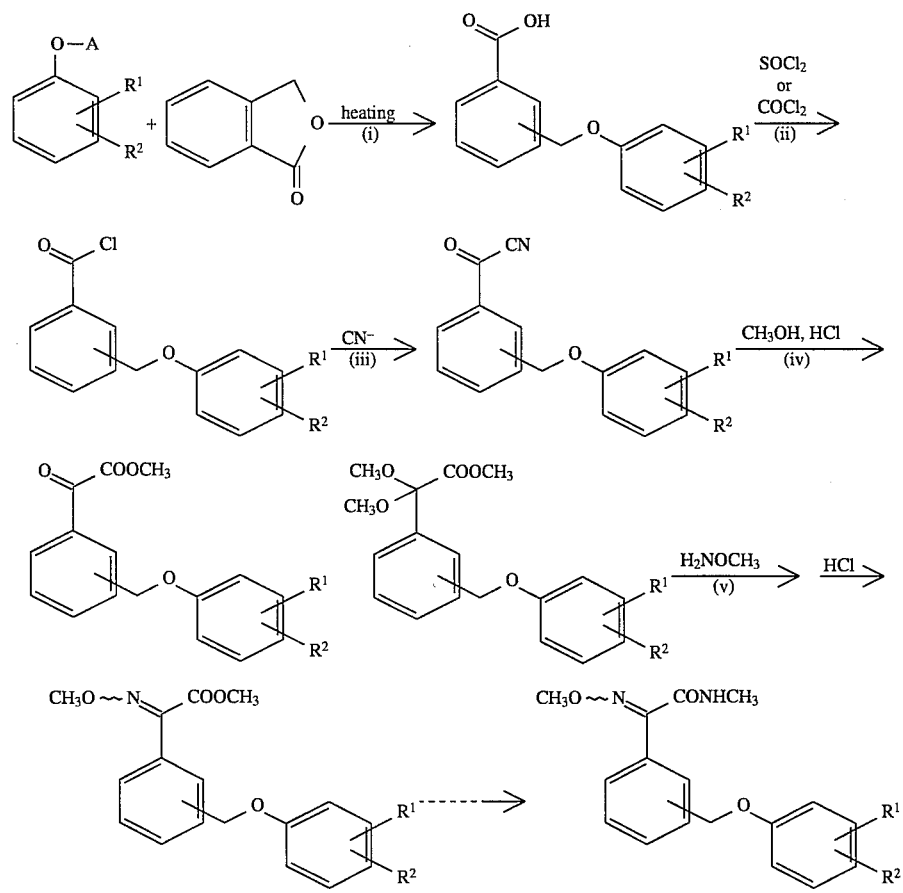

BACKGROUND ART

The carboxylic acid derivatives [VIII] are useful as agricultural fungicides or their intermediates (JP-A 4-295454), and as the process for their production, it has been known that they can be produced by the following route in which metal salts of phenol derivatives of the general formula [I]:

However, when the carboxylic acid derivatives [VIII] are produced by such a process, the reaction in the step (i) is effected at a high temperature such as 200° C., which requires factory facilities for use as a heating source, such as high-pressure steam equipment or high-temperature heat medium control equipment, or the reaction in the step (iv) is effected under cooling below 0° C., which requires various facilities such as freezing machines. This process is, therefore, not a satisfactory process from an industrial point of view.

Further, in this process, different solvents are used in the respective steps: for example, methanol in the step (i); toluene in the steps (ii) and (iii); methyl t-butyl ether and methanol (reaction solvent) as well as dichloromethane (extraction solvent) in the step (iv); and methanol and dichloromethane (reaction solvent) in the step (v). In addition to such a complicated feature that various kinds of solvents are used in the production on an industrial scale, there is another disadvantage that it requires solvent recovery facilities and numerous solvent storage tanks, in which respect the above process is not satisfactory as an industrial production process.

DISCLOSURE OF THE INVENTION

The present inventors have extensively studied to develop an industrially favorable route for production of carboxylic acid derivatives [VIII]. As a result, they have found a quite novel route for production of carboxylic acid derivatives [VIII] where the respective reactions can be allowed to proceed under mild reaction conditions, for example, at temperatures of from room temperature to about 150° C. As a result of further studies, they have found that this route makes it possible to use only one solvent without using various different solvents in the respective steps, thereby completing the present invention.

Thus, the present invention provides a process for producing a carboxylic acid derivative of the general formula [VIII]:

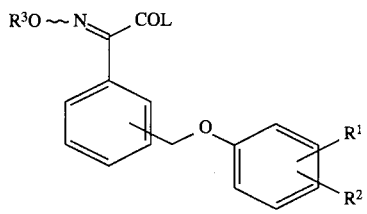

wherein $R^1$, $R^2$ and $R^3$ are each as defined below and L is halogen or $C_1$-$C_5$ alkoxy, characterized in that:
a benzyl halide of the general formula [III]:

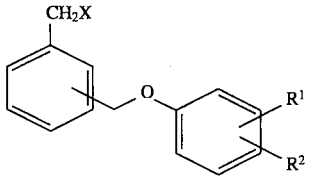

wherein $R^1$ and $R^2$ are the same or different and are independently hydrogen, $C_1$-$C_5$ alkyl, $C_1$-$C_5$ alkoxy, $C_2$-$C_4$ alkenyl, halogen or trifluoromethyl, and X is halogen, is reacted with a cyano compound to give a phenylacetonitrile of the general formula [IV]:

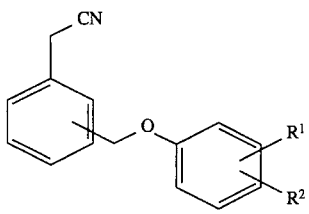

wherein $R^1$ and $R^2$ are each as defined above;
this compound is reacted with an alkyl nitrite in the presence of a base to give an α-hydroxyiminophenylacetonitrile of the general formula [V]:

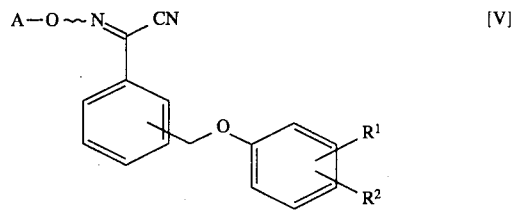

wherein $R^1$ and $R^2$ are each as defined above and A is an alkali metal or an alkaline earth metal;
this compound is reacted with an alkylating agent to give an α-alkoxyiminophenylacetonitrile of the general formula [VI]:

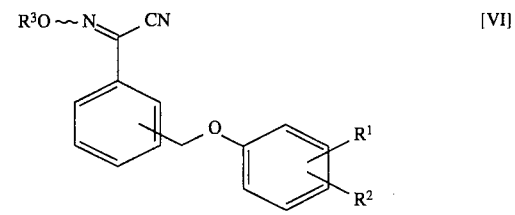

wherein $R^1$ and $R^2$ are each as defined above and $R^3$ is $C_1$-$C_5$ alkyl;
this compound is hydrolyzed in the presence of a base, or this compound is hydrated, treated with an acid and hydrolyzed in the presence of a base, to give an α-alkoxyiminophenylacetic acid of the general formula [VII]:

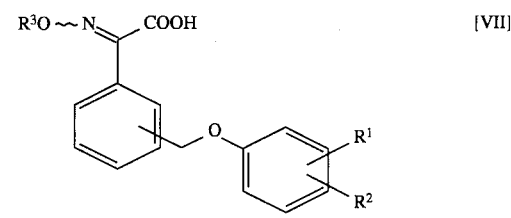

wherein $R^1$, $R^2$ and $R^3$ are each as defined above; and
this compound is reacted with an acid halide forming agent, or this compound is converted into a metal salt and then reacted with an alkylating agent, or this compound is reacted with a lower alcohol in the presence of an acid catalyst.

The benzyl halide [III] can preferably be produced by reacting a metal salt of the phenyl derivative of the general formula [I]:

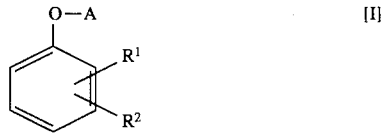

wherein $R^1$, $R^2$ and A are each as defined above, with an α,α'-dihaloxylene derivative of the general formula [II]:

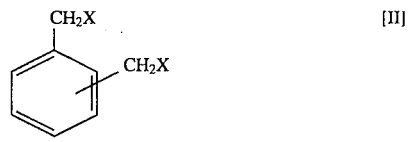

wherein X is as defined above.

The respective steps of the present invention will hereinafter be explained in detail.

First, the following will describe the step of reacting the metal salt of the phenol derivative [I] with the α,α'-dihaloxylene [II] to produce the benzyl halide [III].

As the $R^1$ and $R^2$ in the formula of the metal salt of the phenol derivative [I], there can be mentioned, for example, hydrogen, $C_1$-$C_5$ straight or branched alkyl such as methyl, ethyl, propyl, isopropyl, butyl, sec-butyl, tert-butyl, amyl and tert-amyl; $C_1$-$C_5$ alkoxy such as methoxy, ethoxy, propoxy and butoxy; $C_2$-$C_4$ alkenyl such as ethenyl, propenyl and butenyl; halogen such as fluorine, chlorine and bromine; and trifluoromethyl. As the A, there can be mentioned alkali metals such as sodium and potassium; and alkaline earth metals such as magnesium, calcium and barium.

As the specific examples of the metal salt of the phenol derivative [I], there can be mentioned, for example, sodium, potassium, magnesium, calcium and barium salts of phenol, o-, m- or p-cresol, 2-ethylphenol, 3-ethylphenol, 4-ethylphenol, 2,3-dimethylphenol, 2,4-dimethylphenol, 2,5-dimethylphenol, 2,6-dimethylphenol, 3,4-dimethylphenol, 3,5-dimethylphenol, 2-propylphenol, 4-propylphenol, 2-isopropylphenol, 3-isopropylphenol, 4-isopropylphenol, 2-sec-butylphenol, 4-sec-butylphenol, 2-tert-butylphenol, 3-tert-butylphenol, 4-tert-butylphenol, 4-isopropyl-3-methylphenol, 5-isopropyl-3-methylphenol, 2-tert-butyl-5-methylphenol, 4-tert-amylphenol, 2,4-di-tert-butylphenol, 3,5-di-tert-butylphenol, 2,4-di-tert-amylphenol, 2-methoxy-4-methylphenol, 2-allyl-6-methylphenol, 2-fluorophenol, 4-chlorophenol, 4-bromophenol, 3-chloro-4-fluorophenol, 2-fluoro-6-methoxyphenol, 2-chloro-4-methylphenol, 2-chloro-5-methylphenol, 4-chloro-2-methylphenol, 4-chloro-3-methylphenol, o-, m- or p-trifluoromethylphenol, 2,4-dichlorophenol, and the like.

As the X of the $\alpha,\alpha'$-dihaloxylene derivative [II], there can be mentioned, for example, halogen such as chlorine or bromine. As the specific examples of the $\alpha,\alpha'$-dihaloxylene derivative [II], there can be mentioned $\alpha,\alpha'$-dichloro-o-xylene, $\alpha,\alpha'$-dichloro-m-xylene, $\alpha,\alpha'$-dichloro-p-xylene, $\alpha,\alpha'$-dibromo-o-xylene, $\alpha,\alpha'$-dibromo-m-xylene, $\alpha,\alpha'$-dibromo-p-xylene, and the like.

In this step, the $\alpha,\alpha'$-dihaloxylene derivative [II] is preferably used at an amount of not less than 1.5 moles, particularly 2 to 6 moles, based on the metal salt of the phenol derivative [I], which makes it possible to produce the benzyl halide [III] with ease, with high purity and in high yield.

In the reaction between the metal salt of the phenol derivative [I] and the $\alpha,\alpha'$-dihaloxylene derivative [II], the metal salt of the phenol derivative [I] may be reacted directly with the $\alpha,\alpha'$-dihaloxylene derivative [II], or the metal salt of the phenol derivative [I] may be formed in the reaction system by adding, e.g., dropping, a base to a mixture of the phenol derivative and the dihaloxylene derivative [II] and then reacted with the dihaloxylene derivative.

In the latter procedure, the amount of the alkali metal salt of the phenol derivative [I] can be freely controlled by adjusting the speed of dropping the base, and the reaction can be allowed to proceed while controlling the molar ratio of the metal salt to the $\alpha,\alpha'$-dihaloxylene derivative. As the base, there can be mentioned, for example, sodium hydroxide, potassium hydroxide, sodium carbonate, potassium carbonate, magnesium hydroxide, calcium hydroxide, barium hydroxide, and the like. The amount to be used is in the range of 0.7 to 1.5 equivalents, preferably 0.9 to 1.2 equivalents, to the phenol derivative.

The above reaction is preferably effected in water or in a mixed solvent consisting of an organic solvent and water. As the organic solvent to be used, there can be mentioned, for example, aromatic solvents such as benzene, toluene, xylene, chlorobenzene and o-dichlorobenzene; halogenated hydrocarbons such as chloroform and 1,2-dichloroethane; aliphatic hydrocarbons such as hexane, cyclohexane and heptane; ketones such as acetone and methyl isobutyl ketone; ethers such as diisopropyl ether and methyl t-butyl ether, and the like. As the mixed solvent system consisting of such an organic solvent and water, an aromatic solvent-water system such as toluene-water system is particularly preferred.

The mixing ratio of an organic solvent and water is not particularly limited. It is, however, preferred that the amount of water to be used is such that the halogenated product of the alkali metal formed by the reaction can be dissolved therein.

The amount of the solvent to be used is not particularly limited, and it is usually about 1 to 20 times the weight of the metal salt of the phenol derivative [I].

When the mixed solvent consisting of an organic solvent and water is a heterogeneous system, the addition of a phase transfer catalyst is preferred. As the phase transfer catalyst, there can be mentioned quaternary ammonium salts, quaternary phosphonium salts, and the like. Preferably used are quaternary ammonium salts. As the quaternary ammonium salt, there can be mentioned, for example, tetra-n-butylammonium bromide, benzyltriethylammonium chloride, and the like.

The amount of the phase transfer catalyst to be used is usually 0.001 to 1 time, preferably 0.005 to 0.1 times, the moles of the benzyl halide [III].

In the reaction between the metal salt of the phenol derivative [I] and the $\alpha,\alpha'$-dihaloxylene derivative [II], the reaction temperature is usually 20° C. to 100° C., preferably 40° C. to 90° C., and the reaction time is usually about 0.5 to 20 hours.

The benzyl halide [III] formed can be used as such in the subsequent step; however, for example, it is preferably used in the subsequent step after the removal by distillation of the solvent and the $\alpha,\alpha'$-dihaloxylene derivative present in excess.

When the $\alpha,\alpha'$-dihaloxylene derivative [II] is removed by distillation, it is preferably carried out under reduced pressure in the absence of metals or metal ions, such as iron, aluminum, zinc and tin, which makes it possible to prevent the decomposition of the benzyl halide [III] and the $\alpha,\alpha'$-dihaloxylene derivative. The $\alpha,\alpha'$-dihaloxylene derivative recovered can be used again in the production of benzyl halides without any particular purification.

Thus, the benzyl halide [III] is obtained. As the specific examples thereof, there can be mentioned, for example, 2-(phenoxymethyl)benzyl chloride, 2-(phenoxymethyl)benzyl bromide, 2-(2-methylphenoxymethyl)benzyl chloride, 3-(2-methylphenoxymethyl)benzyl chloride, 4-(2-methylphenoxymethyl)benzyl chloride, 2-(3-methylphenoxymethyl)benzyl chloride, 2-(4-methylphenoxymethyl)benzyl chloride, 2-(2-ethylphenoxymethyl)benzyl chloride, 2-(2-propylphenoxymethyl)benzyl chloride, 2-(2-isopropylphenoxymethyl)benzyl chloride, 2-(2-sec-butylphenoxymethyl)benzyl chloride, 2-(4-tertamylphenoxymethyl)benzyl chloride, 2-(2,3-dimethylphenoxymethyl)benzyl chloride, 2-(2,4-dimethylphenoxymethyl)benzyl chloride, 2-(2,5-dimethylphenoxymethyl)benzyl chloride, 2-(2,6-dimethylphenoxymethyl)benzyl chloride, 2-(3,4-dimethylphenoxymethyl)benzyl chloride, 2-(3,5-dimethylphenoxymethyl)benzyl chloride, 2-(2-methoxyphenoxymethyl)benzyl chloride, 2-(2-propenylphenoxymethyl)benzyl chloride, 2-(3-chloro-4-fluorophenoxymethyl)benzyl chloride, 2-(3-trifluoromethylphenoxymethyl)benzyl chloride, 2-(2-chloro-4-methylphenoxymethyl)benzyl chloride, 2-(2-chloro-5-methylphenoxymethyl)benzyl chloride, 2-(4-chloro-2-methylphenoxymethyl)benzyl chloride, 2-(4-chloro-3-methylphenoxymethyl)benzyl chloride, 2-(2,4-dichlorophenoxymethyl)benzyl chloride, and the like.

Next, the following will describe the step of reacting the benzyl halide [III] with the cyano compound to produce the phenylacetonitrile [IV].

The benzyl halide [III] to be used in this step may include impurities, or of course, it may have high purity.

As the cyano compound, there can be mentioned, for example, sodium cyanide, potassium cyanide, or mixtures thereof. The cyano compound can be used after prepared by reacting hydrogen cyanide with a base such as sodium hydroxide, potassium hydroxide, sodium carbonate, potassium carbonate, magnesium hydroxide, calcium hydroxide or barium hydroxide.

The amount of such a cyano compound to be used is usually 0.8 to 10 times, preferably 1 to 2 times, the moles of the benzyl halide [III].

The reaction is preferably effected in the presence of a mixture consisting of a water-insoluble or hardly water-soluble organic solvent and water. As such a solvent, there can be mentioned, for example, aromatic solvents such as benzene, toluene, xylene, chlorobenzene and o-dichlorobenzene; halogenated hydrocarbons such as dichloromethane and 1,2-dichloroethane; aliphatic hydrocarbons such as hexane and heptane; or mixtures thereof. In particular, toluene-water system is preferably used. The amount of the water-insoluble or hardly water-soluble organic solvent to be used is usually about 1 to 10 times the weight of the benzyl halide [III].

Further, for example, an aprotic polar solvent such as dimethylformamide and dimethylsulfoxide can also be used.

When the mixed solvent consisting of an organic solvent and water is heterogenous, the addition of a phase transfer catalyst is preferred. As the phase transfer catalyst, there can be mentioned quaternary ammonium salts, quaternary phosphonium salts, and the like. Preferably used are quaternary ammonium salts. As the quaternary ammonium salt, there can be mentioned, for example, tetra-n-butylammonium bromide, benzyltriethylammonium chloride, and the like.

The amount of the phase transfer catalyst to be used is usually 0.001 to 1 time, preferably 0.005 to 0.1 times, the moles of the benzyl halide [III].

The reaction temperature is usually 0° C. to 100° C., preferably 60° C. to 90° C., and particularly preferably 70° C. to 85° C., and the reaction time is usually about 0.5 to 20 hours.

Thus, the crude phenylacetonitrile derivative [IV] is formed from the cyano compound and benzyl halide [III]. The product obtained is usually used for the reaction in the subsequent step, as such alter subjected only to water washing, or after the residual cyan is decomposed by treatment with an aqueous solution of a metal salt of hypohalogenous acid.

If necessary, the product can be obtained by concentrating and bringing into dryness under reduced pressure, and then used for the reaction in the subsequent step. Further, it can also be used in the subsequent step after purified by an ordinary purification technique such as distillation, recrystallization or column chromatography.

As the metal salt of hypohalogenous acid to be used for the decomposition of the residual cyan, there can be mentioned, for example, sodium hypochlorite, calcium hypochlorite, and the like. The amount to be used is usually 0.01 to 2 times the moles of the phenylacetonitrile derivative [IV]. The treatment temperature is usually 0° to 80° C., and the treatment time is about 0.1 to 10 hours.

As the phenylacetonitrile [IV] to be obtained in this step, there can be mentioned, for example, 2-(phenoxymethyl)phenylacetonitrile, 2-(2-methylphenoxymethyl)phenylacetonitrile, 3-(2-methylphenoxymethyl)phenylacetonitrile, 4-(2-methylphenoxymethyl)phenylacetonitrile, 2-(3-methylphenoxymethyl)phenylacetonitrile, 2-(4-methylphenoxy-methyl)phenylacetonitrile, 2-(2-ethylphenoxymethyl)phenylacetonitrile, 2-(2-propylphenoxymethyl)phenylacetonitrile, 2-(2-isopropylphenoxymethyl)phenylacetonitrile, 2-(2-sec-butylphenoxymethyl)phenylacetonitrile, 2-(4-tert-amylphenoxymethyl)phenylacetonitrile, 2-(2,3-dimethylphenoxymethyl)phenylacetonitrile, 2-(2,4-dimethylphenoxymethyl)phenylacetonitrile, 2-(2,5-dimethylphenoxymethyl)phenylacetonitrile, 2-(2,6-dimethylphenoxymethyl)phenylacetonitrile, 2-(3,4-dimethylphenoxymethyl)phenylacetonitrile, 2-(3,5-dimethylphenoxymethyl)phenylacetonitrile, 2-(2-methoxyphenoxymethyl)phenylacetonitrile, 2-(2-propenylphenoxymethyl)phenylacetonitrile, 2-(3-chloro-4-fluorophenoxymethyl)phenylacetonitrile, 2-(3-trifluoromethylphenoxymethyl)phenylacetonitrile, 2-(2-chloro-4-methylphenoxymethyl)phenylacetonitrile, 2-(2-chloro- 5-methylphenoxymethyl)phenylacetonitrile, 2-(4-chloro-2-methylphenoxymethyl)phenylacetonitrile, 2-(4-chloro-3-methylphenoxymethyl)phenylacetonitrile, 2-(2,4-dichlorophenoxymethyl)phenylacetonitrile, and the like.

Next, the following will describe the step of reacting the phenylacetonitrile [IV] with the alkyl nitrite in the presence of a base to produce the α-hydroxyiminophenylacetonitrile [V].

As the alkyl nitrite, there can be mentioned, for example, methyl nitrite, ethyl nitrite, n-propyl nitrite, isopropyl nitrite, n-butyl nitrite, amyl nitrite, hexyl nitrite, and the like. Such an alkyl nitrite may be used after synthesized according to the known methods or may be obtained from commercial sources.

The amount of the alkyl nitrite to be used is 0.8 to 10 times, preferably 1 to 2 times, the moles of the phenylacetonitrile [IV].

As the base to be used in this step, there can be mentioned, for example, inorganic bases such as alkali metal hydroxide, e.g., sodium hydroxide and potassium hydroxide; and alkaline earth metal hydroxide, e.g., calcium hydroxide. The use of organic bases such as alkali metal alkoxide, e.g., sodium ethoxide, is also allowed. Two or more kinds of these bases can be used in combination.

The amount of the base to be used is usually 0.8 to 10 equivalents, preferably 1 to 2 equivalents, to the phenylacetonitrile [IV].

The reaction is preferably effected in the presence of a solvent. As the solvent, there can be mentioned, for example, solvents substantially inert to the reaction, such as aromatic solvents, e.g., benzene, toluene, xylene, chlorobenzene and o-dichlorobenzene; aliphatic hydrocarbons, e.g., hexane and heptane; halogenated hydrocarbons e.g., dichloromethane, chloroform and 1,2-dichloroethane; alcohols, e.g., methanol and ethanol; ketones, e.g., acetone, methyl ethyl ketone and methyl isobutyl ketone, and the like. The use of hydrous alcohols is also allowed. Two or more kinds of these solvents can be used in combination. In particular, mixed solvents of the aromatic solvent-alcohol system, such as toluene-methanol and toluene-n-butanol, are preferably used.

The amount of the solvent to be used is usually about 1 to 10 times the weight of the phenylacetonitrile [IV].

The reaction is effected in the presence of a base, usually at 0° C. to the refluxing temperature of the reaction mixture, preferably 0° to 40° C.

The reaction time is usually about 0.5 to 20 hours.

Thus, the reaction mixture containing the α-hydroxyiminophenylacetonitrile [V] as the desired product is obtained. The reaction mixture can be extracted with water to separate the desired product [V] in the aqueous layer from the impurities in the organic layer.

As such impurities, there can be mentioned, for example, the benzyl halide [III]; the α,α'-dihaloxylene derivative [II] combined with two molecules of the metal salt of the phenol derivative [I]; the starting materials and by-products in the production of the α,α'-dihaloxylene derivative [II], and the like, which are derived from the steps (1) and (2). All the impurities can be removed at once in this step without any purification procedure in the steps (1) and (2).

Therefore, to obtain the α-hydroxyiminophenylacetonitrile [V] as the desired product in high purity, the reaction mixture is preferably extracted with water.

In the case of water extraction, water is added to the reaction mixture. When a hydrophilic organic solvent has been used, the reaction mixture is usually used after the removal of the hydrophilic organic solvent by a technique such as concentration.

Water is added so that the total amount thereof becomes usually about 1 to 20 times the weight of the phenylacetonitrile [IV] used.

Further, the addition of a water-insoluble or hardly water-soluble organic solvent is also preferable; for example, aromatic solvents such as benzene, toluene, xylene, chlorobenzene and o-dichlorobenzene; aliphatic hydrocarbons such as hexane and heptane; halogenated hydrocarbons such as dichloromethane and 1,2-dichloroethane; ketones such as methyl isobutyl ketone; ethers such as diethyl ether, and the like. The addition of such an organic solvent makes it possible to separate the impurities with high efficiency.

In that case, the organic solvent is added so that the total amount thereof becomes usually about 0.1 to 5 times the weight of water added.

Further, the aqueous layer separated by the extraction procedure can be washed with a water-insoluble or hardly water-soluble organic solvent.

Then, the aqueous layer containing the α-hydroxyiminophenylacetonitrile [V] is usually supplied as the starting material in the subsequent step without any neutralization.

The α-hydroxyiminophenylacetonitrile [V] may also be converted into its free form of α-hydroxyiminophenylacetonitrile by neutralization with an acid and supplied as the starting material in the subsequent step.

In the neutralization, as the acid to be used, either an organic acid or an inorganic acid may be used, although an inorganic acid is preferably used. As the preferred inorganic acid, there can be mentioned, for example, mineral acids such as hydrochloric acid, sulfuric acid and nitric acid.

The acid is used until the pH of the system becomes 7 or lower, preferably 4 or lower, and more preferably 2 or lower.

The neutralization with an acid is usually effected at −10° to 100° C., preferably 0° to 40° C.

The α-hydroxyiminophenylacetonitrile in free form obtained by neutralization can be isolated, if necessary, and used for the reaction in the subsequent step. That is, the α-hydroxyiminophenylacetonitrile in free form can readily be isolated by filtration when obtained as crystals, or for example, by extraction with an organic solvent, followed by removal of the organic solvent by distillation, when obtained in an oily product. Further, it can also be used in the subsequent step after purified by an ordinary purification technique such as distillation, recrystallization or column chromatography.

As the α-hydroxyiminophenylacetonitrile [V] obtained in this step, there can be mentioned, for example, alkali metal or alkaline earth metal salts of α-hydroxyimino-2-(phenoxymethyl)phenylacetonitrile, α-hydroxyimino-2-(2-methylphenoxymethyl)phenylacetonitrile, α-hydroxyimino-3-(2-methylphenoxymethyl)phenylacetonitrile, α-hydroxyimino- 4-(2-methylphenoxymethyl)phenylacetonitrile, α-hydroxyimino-2-(3-methylphenoxymethyl)phenylacetonitrile, α-hydroxyimino-2-(4-methylphenoxymethyl)phenylacetonitrile, α-hydroxyimino-2-(2-ethylphenoxymethyl)phenylacetonitrile, α-hydroxyimino-2-( 2-propylphenoxymethyl)phenylacetonitrile, α-hydroxyimino-2-(2-isopropylphenoxymethyl)phenylacetonitrile, α-hydroxyimino-2-(2-sec-butylphenoxymethyl)phenylacetonitrile, α-hydroxyimino-2-(4-tert-amylphenoxymethyl)phenylacetonitrile, α-hydroxyimino- 2-(2,3-dimethylphenoxymethyl)phenylacetonitrile, α-hydroxyimino-2-(2,4 -dimethylphenoxymethyl)phenylacetonitrile, α-hydroxyimino-2-(2,5-dimethylphenoxymethyl)phenylacetonitrile, α-hydroxyimino-2-(2,6-dimethylphenoxymethyl)phenylacetonitrile, α-hydroxyimino-2-(3, 4-dimethylphenoxymethyl)phenylacetonitrile, α-hydroxyimino- 2-(3,5-dimethylphenoxymethyl)phenylacetonitrile, α-hydroxyimino-2-(2-methoxyphenoxymethyl)phenylacetonitrile, α-hydroxyimino-2-(2-propenylphenoxymethyl)phenylacetonitrile, α-hydroxyimino-2-(3-chloro-4-fluorophenoxymethyl)phenylacetonitrile, α-hydroxyimino-2-(3-trifluoromethylphenoxymethyl)phenylacetonitrile, α-hydroxyimino- 2-(2-chloro-4-methylphenoxymethyl)phenylacetonitrile, α-hydroxyimino-2-(2-chloro- 5-methylphenoxymethyl)phenylacetonitrile, α-hydroxyimino-2-(4-chloro-2-methylphenoxymethyl)phenylacetonitrile, α-hydroxyimino-2-(4-chloro-3-methylphenoxymethyl)phenylacetonitrile, α-hydroxyimino-2-(2,4-dichlorophenoxymethyl)phenylacetonitrile, and the like.

The α-hydroxyiminophenylacetonitrile [V] formed by this reaction is a mixture of E and Z isomers. The ratio of these E/Z isomers can be changed by the reaction conditions, although the Z isomer is usually the main product.

Next, the following will describe the step of reacting the α-hydroxyiminophenylacetonitrile [V] with an alkylating agent to produce the α-alkoxyiminophenylacetonitrile [VI].

In this step, when the α-hydroxyiminophenylacetonitrile in free form is used, it is usually used alter converted into its alkali metal or alkaline earth metal salt.

As the alkylating agent, there can be mentioned alkyl halides, dialkyl sulfates, and the like of the general formula: $R^4$-Y wherein $R^4$ is $C_1$-$C_5$ alkyl and Y is halogen or $OSO_3R^3$.

As the $R^4$, there can be mentioned, for example, $C_1$-$C_5$ lower alkyl such as methyl, ethyl, propyl, isopropyl, butyl and amyl.

As the typical examples of the alkyl halides, there can be mentioned, for example, methyl chloride, methyl bromide, methyl iodide, and the like.

As the typical example of the dialkyl sulfates, there can be mentioned, for example, dimethyl sulfate, diethyl sulfate, and the like.

The amount of such an alkylating agent is usually 0.9 to 3 times, preferably 1.0 to 1.5 times, to one mole of the α-hydroxyiminophenylacetonitrile [V].

In this step, the reaction between the α-hydroxyiminophenylacetonitrile [V] and the alkylating agent is preferably effected using a mixed solvent system consisting of a hydrocarbon solvent and water in the presence of a phase transfer catalyst, which makes it possible to reduce the formation of a nitron derivative as the by-product. As the hydrocarbon solvent, there can be mentioned, for example, aromatic solvents such as benzene, toluene, xylene chlorobenzene and o-dichlorobenzene; and aliphatic solvents such as hexane and heptane. In usual cases, aromatic solvents such as toluene are preferably used. The amount of the solvent to be used is usually about 1 to 10 times the weight of the α-hydroxyiminophenylacetonitrile [V] . The amount of the water to be used is usually about 1 to 10 times the weight of the α-hydroxyiminophenylacetonitrile [V].

As the phase transfer catalyst, there can be mentioned quaternary ammonium salts, quaternary phosphonium salts, and the like. Preferably used are quaternary ammonium salts. As the quaternary ammonium salts, there can be mentioned, for example, tetra-n-butylammonium bromide, benzyltriethylammonium chloride, and the like.

The amount of the phase transfer catalyst to be used is usually 0.001 to 1 time, preferably 0.005 to 0.1 times, the moles of the α-hydroxyiminophenylacetonitrile [V].

In the reaction of the α-hydroxyiminophenylacetonitrile [V] as the starting material and the alkylating agent, there is no particular limitation to the order or method for addition. The maintenance of a higher ratio of the phase transfer catalyst to the α-hydroxyiminophenylacetonitrile [V] makes it possible to improve the yield and to reduce the formation of a nitron compound as the by-product. More specifically, the reaction is preferably effected by the method in which the phase transfer catalyst is added in a solvent containing the alkylating agent, to which the α-hydroxyiminophenylacetonitrile derivative [V] or its solution is then added dropwise or added in portions while keeping the pH of the reaction system to 9 to 14, preferably 11 to 13; some part of the alkylating agent is added to a solvent containing the phase transfer catalyst, and the α-hydroxyiminophenylacetonitrile derivative [V] or its solution is then added dropwise or added in portions while keeping the pH of the reaction system to 9 to 14, preferably 11 to 13, during which the other part of the alkylating agent is appropriately added in portions; the alkylating agent and the α-hydroxyiminophenylacetonitrile derivative [V] or its solution are simultaneously added dropwise to a solvent containing the phase transfer catalyst while keeping the pH of the reaction system to 9 to 14, preferably 11 to 13; or the like.

The reaction temperature is usually 0° to 60° C., preferably 10° to 40° C., and the reaction time is usually about 0.5 to 20 hours.

As to the α-alkoxyiminophenylacetonitrile derivative [VI] formed, the reaction mixture is usually subjected to phase separation to remove the aqueous layer, and the organic layer is washed with a base such as an aqueous sodium hydroxide solution and then used as such for the reaction in the subsequent step. When the organic layer is colored, decolorization can be effected by washing the organic layer with a base and then treating with an aqueous solution of a metal salt of hypohalogenous acid.

As the aqueous solution of the metal salt of hypohalogenous acid to be used in the decolorization, there can be mentioned, for example, sodium hypochlorite, calcium hypochlorite, and the like. The amount to be used is usually 0.01 to 2 times the moles of the α-alkoxyiminophenylacetonitrile derivative [VI]. The treatment temperature is usually 0° to 80° C., and the treatment time is about 0.1 to 10 hours.

Also, the α-alkoxyiminophenylacetonitrile derivative [VI] can be obtained by concentrating and bringing into dryness under reduced pressure, if necessary, and used for the reaction in the subsequent step. Further, it can also be used in the subsequent step after purified by an ordinary purification technique such as distillation, recrystallization or column chromatography.

As the specific examples of the α-alkoxyiminophenylacetonitrile [VI] obtained in this step, there can be mentioned, for example, α-methoxyimino-2-(phenoxymethyl)phenylacetonitrile, α-methoxyimino-2-(2-methylphenoxymethyl)phenylacetonitrile, α-methoxyimino-3-(2-methylphenoxymethyl)phenylacetonitrile, α-methoxyimino- 4-(2-methylphenoxymethyl)phenylacetonitrile, α-methoxyimino-2-(3-methylphenoxymethyl)phenylacetonitrile, α-methoxyimino-2-(4-methylphenoxymethyl)phenylacetonitrile, α-methoxyimino-2-(2-ethylphenoxymethyl)phenylacetonitrile, α-methoxyimino- 2-(2-propylphenoxymethyl)phenylacetonitrile, α-methoxyimino-2-(2-isopropylphenoxymethyl)phenylacetonitrile, α-methoxyimino-2-(2-sec-butylphenoxymethyl)phenylacetonitrile, α-methoxyimino-2-(4-tert-amylphenoxymethyl)phenylacetonitrile, α-methoxyimino- 2-(2,3-dimethylphenoxymethyl)phenylacetonitrile, α-methoxyimino-2-(2,4 -dimethylphenoxymethyl)phenylacetonitrile α-methoxyimino-2-(2,5-dimethylphenoxymethyl)phenylacetonitrile, α-methoxyimino-2-(2,6-dimethylphenoxymethyl)phenylacetonitrile, α-methoxyimino-2-(3,4-dimethylphenoxymethyl)phenylacetonitrile, α-methoxyimino-2-(3,5-dimethylphenoxymethyl)phenylacetonitrile, α-methoxyimino-2-(2-methoxyphenoxymethyl)phenylacetonitrile, α-methoxyimino-2-(2-propenylphenoxymethyl)phenylacetonitrile, α-methoxyimino-2-(3-chloro-4-fluorophenoxymethyl)phenylacetonitrile, α-methoxyimino-2-(3-trifluoromethylphenoxymethyl)phenylacetonitrile, α-methoxyimino- 2-(2-chloro-4-methylphenoxymethyl)phenylacetonitrile, α-methoxyimino-2-(2-chloro- 5-methylphenoxymethyl)phenylacetonitrile, α-methoxyimino-2-(4-chloro-2 -methylphenoxymethyl)phenylacetonitrile, α-methoxyimino-2-(4-chloro-3-methylphenoxymethyl)phenylacetonitrile, α-methoxyimino-2-(2,4-dichlorophenoxymethyl)phenylacetonitrile, α-ethoxyimino-(2-phenoxymethyl)phenylacetonitrile, α-ethoxyimino-2-(2-methylphenoxymethyl)phenylacetonitrile, α-ethoxyimino-2-(2,5-dimethylphenoxymethyl)phenylacetonitrile, α-ethoxyimino-2-(4-chloro-2-methylphenoxymethyl)phenylacetonitrile, α-ethoxyimino-2-(3-trifluoromethylphenoxymethyl)phenylacetonitrile, and the like.

Next, the following will describe the step of treating the α-alkoxyiminophenylacetonitrile [VI] with a base for hydrolysis to produce the α-alkoxyiminophenylacetic acid [VII].

As the base, there can be mentioned, for example, hydroxides of alkali metals, such as sodium hydroxide and potassium hydroxide; hydroxides of alkaline earth metals, such as calcium hydroxide, and the like. In these bases, potassium hydroxide is preferred.

The amount of the base to be used is usually 0.8 to 10 times, preferably 1.2 to 2.5 times, the equivalents of the α-alkoxyiminophenylacetonitrile [VI].

This reaction is usually effected in water or in a mixed solvent consisting of an organic solvent and water. As such a solvent, there can be mentioned, for example, solvents substantially inert to the reaction, such as aromatic solvents, e.g., benzene, toluene, xylene, chlorobenzene and o-dichlorobenzene; alcohols, e.g., methanol and ethanol; aliphatic hydrocarbons, e.g., hexane and heptane; halogenated hydrocarbons, e.g., dichloromethane and chloroform; ethers, e.g., diisopropyl ether and methyl t-butyl ether; ketones, e.g., acetone and methyl isobutyl ketone, and the like. Two or more kinds of these solvents can be used in combination. Preferably, aromatic solvent-alcohol-water systems such as a mixed system of toluene-methanol-water are used.

The amount of the solvent to be used is usually about 1 to 10 times the weight of the α-alkoxyiminophenylacetonitrile [VI]. In the mixed system of toluene-methanol-water, for example, the amounts of toluene, methanol and water are preferably 1.5 to 2.5 times, 0.5 to 1.0 time and 0.3 to 0.8 times, respectively, the weight of the α-alkoxyiminophenylacetonitrile [VI].

The reaction temperature is usually 20° to 100° C., and the reaction time is about 1 to 60 hours. Although the reaction can be effected under normal or increased pressure, it is usually effected under normal pressure.

The mixed solution containing the α-alkoxyiminophenylacetic acid [VII] obtained usually used in the subsequent step after an acid such as hydrochloric acid is added to make it acidic to extract the phenylacetic acid [VII] into the organic layer, followed by phase separation to remove the aqueous layer. Also, if necessary, the phenylacetic acid [VII] can be isolated by concentrating the organic layer and bringing it into dryness. Further, it may be used in the subsequent step after purified by a purification technique which is usually used.

In some cases, the mixed solution containing the α-alkoxyiminophenylacetic acid [VII] can also be used as such in the subsequent step.

As the α-alkoxyiminophenylacetic acid [VII] thus obtained, there can be mentioned, for example, α-methoxyimino-2-(phenoxymethyl)phenylacetic acid, α-methoxyimino- 2-(2-methylphenoxymethyl)phenylacetic acid, α-methoxyimino-3-(2-methylphenoxymethyl)phenylacetic acid, α-methoxyimino-4-(2-methylphenoxymethyl)phenylacetic acid, α-methoxyimino-2-(3-methylphenoxymethyl)phenylacetic acid, α-methoxyimino-2-( 4-methylphenoxymethyl)phenylacetic acid, α-methoxyimino-2-(2-ethylphenoxymethyl)phenylacetic acid, α-methoxyimino-2-(2-propylphenoxymethyl)phenylacetic acid, α-methoxyimino- 2-(2-isopropylphenoxymethyl)phenylacetic acid, α-methoxyimino-2-(2-secbutylphenoxymethyl)phenylacetic acid, α-methoxyimino-2-(4-tert-amylphenoxymethyl)phenylacetic acid, α-methoxyimino-2-(2,3-dimethylphenoxymethyl)phenylacetic acid, α-methoxyimino-2-(2,4-dimethylphenoxymethyl)phenylacetic acid, α-methoxyimino-2-( 2,5-dimethylphenoxymethyl)phenylacetic acid, α-methoxyimino-2-(2,6-dimethylphenoxymethyl)phenylacetic acid, α-methoxyimino-2-(3, 4-dimethylphenoxymethyl)phenylacetic acid, α-methoxyimino-2-(3,5-dimethylphenoxymethyl)phenylacetic acid, α-methoxyimino- 2-(2-methoxyphenoxymethyl)phenylacetic acid, α-methoxyimino-2-(2-propenylphenoxymethyl)phenylacetic acid, α-methoxyimino-2-(3-chloro-4-fluorophenoxymethyl)phenylacetic acid, α-methoxyimino-2-(3-trifluoromethylphenoxymethyl)phenylacetic acid, α-methoxyimino-2-(2-chloro-4-methylphenoxymethyl)phenylacetic acid, α-methoxyimino-2-(2-chloro-5-methylphenoxymethyl)phenylacetic acid, α-methoxyimino- 2-(4-chloro-2-methylphenoxymethyl)phenylacetic acid, α-methoxyimino-2-(4-chloro- 3-methylphenoxymethyl)phenylacetic acid, α-methoxyimino-2-(2, 4-dichlorophenoxymethyl)phenylacetic acid, α-ethoxyimino-2-(phenoxymethyl)phenylacetic acid, α-ethoxyimino-2-(2-methylphenoxymethyl)phenylacetic acid, α-ethoxyimino-2-(2,5 -dimethylphenoxymethyl)phenylacetic acid, α-ethoxyimino-2-(4-chloro-2-methylphenoxymethyl)phenylacetic acid, α-ethoxyimino-2-(3-trifluoromethylphenoxymethyl)phenylacetic acid, and the like.

Next, the following will describe the step of producing the carboxylic acid derivative [VIII] as the desired product from the α-alkoxyiminophenylacetic acid [VII].

As the L in the carboxylic acid derivative [VIII], there can be mentioned, for example, halogen such as fluorine, chlorine and bromine; and lower alkoxy such as methoxy, ethoxy, propoxy and butoxy.

In the case where L is halogen, there can be mentioned, for example, α-alkoxyiminophenylacetyl halide [X] such as α-methoxyimino-2-(phenoxymethyl)phenylacetyl chloride, α-methoxyimino-2-(2-methylphenoxymethyl)phenylacetyl chloride, α-methoxyimino-3-(2-methylphenoxymethyl)phenylacetyl chloride, α-methoxyimino- 4-(2-methylphenoxymethyl)phenylacetyl chloride, α-methoxyimino-2-(3-methylphenoxymethyl)phenylacetyl chloride, α-methoxyimino-2-(4-methylphenoxymethyl) phenylacetyl chloride, α-methoxyimino-2-(2-ethylphenoxymethyl)phenylacetyl chloride, α-methoxyimino-2-(2-propylphenoxymethyl)phenylacetyl chloride, α-methoxyimino-2-( 2-isopropylphenoxymethyl)phenylacetyl chloride, α-methoxyimino-2-(2-sec-butylphenoxymethyl)-phenylacetyl chloride, α-methoxyimino-2-(4-tert-amylphenoxymethyl)phenylacetyl chloride, α-methoxyimino-2-(2,3 -dimethylphenoxymethyl)phenylacetyl chloride, α-methoxyimino-2-(2, 4-dimethylphenoxymethyl)phenylacetyl chloride, α-methoxyimino- 2-(2,5-dimethylphenoxymethyl)phenylacetyl chloride, α-methoxyimino-2-(2,6-dimethylphenoxymethyl)phenylacetyl chloride, α-methoxyimino-2-(3, 4-dimethylphenoxymethyl)phenylacetyl chloride, α-methoxyimino-2-(3,5-dimethylphenoxymethyl)phenylacetyl chloride, α-methoxyimino-2-(2-methoxyphenoxymethyl)phenylacetyl chloride, α-methoxyimino-2-(2-propenylphenoxymethyl)phenylacetyl chloride, α-methoxyimino-2-(3-chloro-4-fluorophenoxymethyl)phenylacetyl chloride, α-methoxyimino-2-(3 -trifluoromethylphenoxymethyl)phenylacetyl chloride, α-methoxyimino-2-(2-chloro-4-methylphenoxymethyl)phenylacetyl chloride, α-methoxyimino-2-(2-chloro-5-methylphenoxymethyl)phenylacetyl chloride, α-methoxyimino-2-(4-chloro-2-methylphenoxymethyl)phenylacetyl chloride, α-methoxyimino-2-(4-chloro-3-methylphenoxymethyl)phenylacetyl chloride, α-methoxyimino-2-(2,4-dichlorophenoxymethyl)phenylacetyl chloride, α-ethoxyimino-2-(phenoxymethyl)phenylacetyl chloride, α-ethoxyimino-2-(2-methylphenoxymethyl)phenylacetyl chloride, α-ethoxyimino-2-(2,5-dimethylphenoxymethyl)phenylacetyl chloride, α-ethoxyimino-2-(4-chloro-2-methylphenoxymethyl)phenylacetyl chloride and α-ethoxy-imino-2-(3-trifluoromethylphenoxymethyl)phenylacetyl chloride.

Also, in the case where L is lower alkoxy, there can be mentioned, for example, α-alkoxyiminophenylacetic acid esters [XI] such as methyl α-methoxyimino-2-(phenoxymethyl)phenyl acetate, methyl α-methoxyimino-2-(2-methylphenoxymethyl)phenyl acetate, methyl α-methoxyimino-3-(2-methylphenoxymethyl)phenyl acetate, methyl α-methoxyimino-4-(2-methylphenoxymethyl)phenyl acetate, methyl α-methoxyimino- 2-(3-methylphenoxymethyl)phenyl acetate, methyl α-methoxyimino-2-(4-methylphenoxymethyl)phenyl acetate, methyl α-methoxyimino-2-(2-ethylphenoxymethyl)phenyl acetate, methyl α-methoxyimino-2-(2-propylphenoxymethyl)phenyl acetate, methyl α-methoxyimino-2-(2-isopropylphenoxymethyl)phenyl acetate, methyl α-methoxyimino- 2-(2-sec-butylphenoxymethyl)phenyl acetate, methyl α-methoxyimino-2-(4-tert-amylphenoxymethyl)phenyl acetate, methyl α-methoxyimino-2-(2,3-dimethylphenoxymethyl)phenyl acetate, methyl α-methoxyimino-2-(2,4-dimethylphenoxymethyl)phenyl acetate, methyl α-methoxyimino-2-(2,5-dimethylphenoxymethyl)phenyl acetate, methyl α-methoxyimino- 2-(2,6-dimethylphenoxymethyl)phenyl acetate, methyl α-methoxyimino-2-( 3,4-dimethylphenoxymethyl)phenyl acetate, methyl α-methoxyimino-2-(3,5-dimethylphenoxymethyl)phenyl acetate, methyl α-methoxyimino-2-(2-methoxyphenoxymethyl)phenyl acetate, methyl α-methoxyimino-2-(2-propenylphenoxymethyl)phenyl acetate, methyl α-methoxyimino-2-(3-chloro-4-fluorophenoxymethyl)phenyl acetate, methyl α-methoxyimino-2-(3-trifluoromethylphenoxymethyl)phenyl acetate, methyl α-methoxyimino- 2-(2-chloro-4-methylphenoxymethyl)phenyl acetate, methyl α-methoxyimino-2-(2-chloro-5-methylphenoxymethyl)phenyl acetate, methyl α-methoxyimino-2-(4-chloro-2-methylphenoxymethyl)phenyl acetate, methyl α-methoxyimino-2-(4-chloro-3-methylphenoxymethyl)phenyl acetate, methyl α-methoxyimino-2-(2,4-dichlorophenoxymethyl)phenyl acetate, ethyl α-methoxyimino-2-(phenoxymethyl)phenyl acetate, ethyl α-methoxyimino- 2-(2-methylphenoxymethyl)phenyl acetate, ethyl α-methoxyimino-2-(2,5-dimethylphenoxymethyl)phenyl acetate, ethyl α-methoxyimino-2-(3-trifluoromethylphenoxymethyl)phenyl acetate, ethyl α-methoxyimino-2-(4-chloro-2-methylphenoxymethyl)phenyl acetate, butyl α-methoxyimino-2-(phenoxymethyl)phenyl acetate, butyl α-methoxyimino- 2-(2-methylphenoxymethyl)phenyl acetate, butyl α-methoxyimino-2-(2,5-dimethylphenoxymethyl)phenyl acetate, butyl α-methoxyimino-2-(3-trifluoromethylphenoxymethyl)phenyl acetate and butyl α-methoxyimino-2-(4-chloro-2-methylphenoxymethyl)phenyl acetate.

First, when the carboxylic acid derivative [VIII] is the α-alkoxyiminophenylacetyl halide [X], it is produced by reacting the α-alkoxyiminophenylacetic acid [VII] with an acid halide forming agent.

As the acid halide forming agent, there can be mentioned, for example, phosgene, thionyl chloride, oxalyl chloride, phosphorus trichloride, and the like. Preferably used is phosgene which can suppress the formation of impurities.

The amount of the acid halide forming agent to be used is 0.8 to 10 times, preferably 1 to 2 times, the moles of the α-alkoxyiminophenylacetic acid [VII].

The reaction is preferably effected in the presence of a solvent. As the solvent to be used, there can be mentioned, for example, solvents substantially inert to the reaction, such as aromatic solvents, e.g., benzene, toluene, xylene, chlorobenzene and o-dichlorobenzene; halogenated hydrocarbons, e.g., dichloromethane, chloroform and 1,2-dichloroethane; aliphatic hydrocarbons, e.g., hexane and heptane, and the like. Preferably used are aromatic solvents such as toluene. Two or more kinds of these solvents can be used in combination.

The amount of the solvent to be used is usually about 1 to 10 times the weight of the α-alkoxyiminophenylacetic acid [VII].

The reaction is preferably effected in the presence of a catalyst. As such a catalyst, there can be mentioned, for example, dimethylformamide, pyridine, 4-dimethylaminopyridine, N-methylpyrrolidone, and the like.

The amount of the catalyst to be used is usually about 0.005 to 0.2 times the moles of the α-alkoxyiminophenylacetic acid [VII].

The reaction temperature is usually 0° to 100° C., and the reaction time is about 0.5 to 20 hours.

The α-alkoxyiminophenylacetyl halide [X] can be obtained as a mixture of two isomers, i.e., E and Z isomers. Although the E and Z isomers are derived from the previous step, there usually proceeds isomerization of the Z form to the E form in this reaction, and the E isomer can be obtained with high selectivity. Further, the ratio of the E/Z isomers can be changed by the reaction conditions.

The α-alkoxyiminophenylacetyl halide [X] formed can be used for the reaction in the subsequent step, as such or after the acid halide forming agent used in excess is removed by a technique such as concentration. Further, if necessary, it can also be used in the subsequent step after purified by an ordinary purification technique.

Also, when the carboxylic acid derivative [VIII] is the α-alkoxyiminophenyl acetic acid ester [XI], it is produced by converting the α-alkoxyiminophenylacetic acid [VII] into its metal salt, followed by reaction with an alkylating agent, or by reacting the α-alkoxyiminophenylacetic acid [VII] with a lower alcohol in the presence of an acid catalyst.

First, in the case where the α-alkoxyiminophenyl acetic acid ester [XI] is produced by converting the α-alkoxyiminophenylacetic acid [VII] into its metal salt, followed by reaction with an alkylating agent, as the inorganic base to be used for conversion into the metal salt, there can be mentioned, for example, hydroxides of alkali metals or alkaline earth metals, such as sodium hydroxide, potassium hydroxide, calcium hydroxide and barium hydroxide; carbonates of alkali metals or alkaline earth metals, such as sodium carbonate, potassium carbonate and calcium carbonate; bicarbonates of alkali metals, such as sodium bicarbonate and potassium bicarbonate, and the like.

The amount of the inorganic base to be used is usually 0.7 to 3 times, preferably 0.9 to 2 times, the moles of the α-alkoxyiminophenylacetic acid [VII].

As the alkylating agent, there can be mentioned those which are as described above, such as dialkyl sulfates, lower alkyl halides, and the like.

The reaction is preferably in the presence of a solvent. As the solvent to be used, there can be mentioned, for example, aromatic solvents such as benzene, toluene, xylene, chlorobenzene and o-dichlorobenzene; halogenated hydrocarbons such as chloroform and dichloromethane; aliphatic hydrocarbons such as hexane and heptane; ethers such as diisopropyl ether and methyl t-butyl ether; ketones such as acetone and methyl isobutyl ketone; alcohols such as methanol, ethanol, propanol, isopropanol, n-butanol, sec-butanol and t-butanol; water, and the like. Two or more kinds of these solvents can be used in combination. As the solvent system to be preferably used, there can be mentioned, for example, aromatic solvent-water systems such as toluene-water system.

The amount of the solvent to be used is usually 1 to 20 times the weight of the α-alkoxyiminophenylacetic acid [VII].

The reaction temperature is usually 0° to 100° C., preferably 5° to 60° C., and the reaction time is usually about 0.5 to 20 hours.

Next, in the case where the α-alkoxyiminophenyl acetic acid ester [XI] is produced by reacting the α-alkoxyiminophenylacetic acid [VII] with a lower alcohol in the presence of an acid catalyst, as the acid catalyst, there can be mentioned, for example, sulfuric acid, hydrogen chloride, toluenesulfonic acid, methanesulfonic acid, and the like. The amount of the acid catalyst to be used is usually about 0.01 to 5 times the moles of the α-alkoxyiminophenylacetic acid [VII].

Also, as the lower alcohol, used are alcohols of the general formula: $R^5$-OH. As the $R^5$, there can be mentioned, for example, $C_1$-$C_5$ alkyl groups such as methyl, ethyl, propyl, isopropyl, butyl and sec-butyl. As the typical examples thereof, there can be mentioned, for example, methanol, ethanol, and the like. The amount of the lower alcohol to be used is usually about 1 to 10 times the weight of the α-alkoxyiminophenylacetic acid [VII].

The reaction is usually effected in the presence of a solvent. As the solvent to be used, there can be mentioned, for example, aromatic solvents such benzene, toluene, xylene, chlorobenzene and o-dichlorobenzene; halogenated hydrocarbons such as dichloromethane and 1,2-dichloroethane; aliphatic hydrocarbons such as hexane and heptane, and the like. Preferably used are aromatic solvents such as toluene. Two or more kinds of these solvents can be used in combination. Also, lower alcohols and the like, which are the same as the reagents, can be used.

The amount of the solvent to be used is usually about 1 to 10 times the weight of the α-alkoxyiminophenylacetic acid [VII].

The reaction temperature is usually 0° to 100° C., preferably 20° to 60° C., and the reaction time is about 0.5 to 40 hours.

The α-alkoxyiminophenyl acetic acid ester [XI] can also be produced by reacting the α-alkoxyiminophenylacetyl halide [X] with a lower alcohol.

As the lower alcohol, there can be mentioned those compounds which are as described above. The amount to be used is usually 0.8 to 10 times, preferably 0.9 to 2 times, the moles of the α-alkoxyiminophenylacetyl halide [X].

The reaction is preferably effected in the presence of a solvent. As the solvent to be used, there can be mentioned, for example, aromatic solvents such as benzene, toluene, xylene, chlorobenzene and o-dichlorobenzene; halogenated hydrocarbons such as dichloromethane, chloroform and 1,2-dichloroethane; aliphatic hydrocarbons such as hexane and heptane; ethers such as diisopropyl ether and methyl t-butyl ether, and the like. Two or more kinds of these solvents can be used in combination. Further, lower alcohols such as methanol and ethanol, which are also the reagents as described above, can be used.

The amount of the solvent to be used is usually about 1 to 10 times the weight of the α-alkoxyiminophenylacetyl halide [X].

To the reaction system, a base may be added, if necessary. As the base to be used, there can be mentioned, for example, tertiary amines such as triethylamine, pyridine and N,N-diethylaniline.

When the base is added, the amount to be used is usually about 0.7 to 3 times the moles of the α-alkoxyiminophenylacetyl halide [X].

The reaction temperature is usually 0° to 100° C., preferably 10° to 40° C., and the reaction time is about 0.5 to 20 hours.

The α-alkoxyiminophenyl acetic acid ester [XI] can also be derived from the α-alkoxyiminophenylacetonitrile [VI].

As the method therefor, there can be mentioned the following processes: the α-alkoxyiminophenylacetonitrile [VI] is reacted with a lower alcohol in the presence of an acid catalyst, followed by reaction with water (e.g., SURVEY OF ORGANIC SYNTHESIS, 1970, p.813 (John Wiley & Sons, Inc.)); or the α-alkoxyiminophenylacetonitrile [VI] is hydrated to give an α-alkoxyiminophenylacetamide which is isomerized into the E isomer by treatment with an acid, followed by hydrolysis in the presence of a base to give the α-alkoxyiminophenylacetic acid [VII] which is reacted with an alkylating agent.

Now, the following will describe the process for producing the α-alkoxyiminophenyl acetic acid ester [XI] by way of the α-alkoxyiminophenylacetamide.

In the hydration of the α-alkoxyiminophenylacetonitrile [VI], a base is preferably used. As the base, there can be mentioned, for example, hydroxides of alkali metals, such as sodium hydroxide and potassium hydroxide; hydroxides of alkaline earth metals, such as calcium hydroxide, and the like. In these bases, potassium hydroxide is preferably used.

The amount of the base to be used is usually 0.8 to 10 equivalents, preferably 0.9 to 2.0 equivalents, to the α-alkoxyiminophenylacetonitrile [VI].

As the acid to be used in the isomerization, there can be used, for example, hydrohalogenic acids, hydrogen halide, sulfonic acids, and Lewis acids.

As the hydrohalogenic acids, there can be mentioned, for example, hydrochloric acid, hydrobromic acid, hydroiodic acid, and the like. As the hydrogen halides, there can be mentioned, for example, hydrogen chloride, hydrogen bromide, hydrogen iodide, and the like. As the sulfonic acids, there can be mentioned, for example, aliphatic sulfonic acids such as trifluoromethanesulfonic acid; aromatic sulfonic acids such as toluenesulfonic acid, and the like. As the Lewis acids, there can be mentioned, for example, titanium tetrachloride, titanium trichloride, and the like.

The amount of the acid to be used is usually 0.005 to 10 times, preferably 0.05 to 3 times, the moles of the α-alkoxyiminophenylacetamide (the total moles of the E and Z isomers).

As the base to be used in the hydrolysis, there can be mentioned, for example, those which are as described above. The amount of the base to be used is usually 0.8 to 10 equivalents, preferably 0.9 to 2.0 equivalents, to the α-alkoxyiminophenylacetamide (the total moles of the E and Z isomers).

The respective reactions are preferably in the presence of a solvent. As the solvent to be used, there can be mentioned, for example, solvents substantially inert to the reactions, such as aromatic solvents, e.g., benzene, toluene, xylene, chlorobenzene and o-dichlorobenzene; alcohols, e.g. methanol and ethanol; halogenated hydrocarbons, e.g., dichloromethane, chloroform and 1,2-dichloroethane; aliphatic hydrocarbons, e.g., hexane and heptane; ethers, e.g., diisopropyl ether and methyl t-butyl ether; ketones, e.g., acetone and methyl isobutyl ketone; water, and the like. Two or more kinds of these solvents can be used in combination.

The amount of the solvent to be used is usually about 1 to 20 times the weight of the reagents used.

The reaction temperature is usually 20° to 100° C. for the hydration, 0° to 100° C. for the isomerization, 20° to 100° C. for the hydrolysis and 0° to 100° C. for alkylation, and the reaction time is usually about 0.5 to 40 hours for the respective reactions.

As to the α-alkoxyiminophenyl acetic acid ester [XI] formed by the respective processes as described above, after evaporation of alcohols in case where the reaction solution contains the alcohols, the reaction mixture is extracted with a water-insoluble organic solvent as described above, such as an aromatic solvent or a halogenated hydrocarbon. The organic layer is washed with water and then with an acid such as diluted hydrochloric acid, after which it can be used for the reaction in the subsequent step, as such or after concentration, if necessary. Further, it can also be used in the subsequent step after purified by an ordinary purification technique, if necessary.

The acetic acid ester [XI] thus obtained can be usually obtained as a mixture of two isomers, i.e., E and Z isomers. The Z isomer can readily be isomerized into the E isomer by addition of an acid to the solution obtained by the respective processes as described above.

As the acid to be used in the isomerization, there can be used, for example, hydrohalogenic acids, hydrogen halides, sulfonic acids, and Lewis acids.

As the hydrohalogenic acids, there can be mentioned, for example, hydrochloric acid, hydrobromic acid, hydroiodic acid, and the like. As the hydrogen halides, there can be mentioned, for example, hydrogen chloride, hydrogen bromide, hydrogen iodide, and the like. As the sulfonic acids, there can be mentioned, for example, aliphatic sulfonic acid such as trifluoromethanesulfonic acid; aromatic sulfonic acid such as toluene sulfonic acid, and the like. As the Lewis acids, there can be mentioned, for example, titanium tetrachloride, titanium trichloride, and the like.

The amount of the acid to be used is usually 0.005 to 10 times, preferably 0.05 to 3 times, the moles of the acetic acid ester [XI] (the total moles of the E and Z isomers).

Also, as the solvent used in the isomerization, there can be mentioned, for example, aromatic solvents such as benzene, toluene, xylene, chlorobenzene and o-dichlorobenzene; halogenated hydrocarbons such as dichloromethane, chloroform and 1,2-dichloroethane; aliphatic hydrocarbons such as hexane and heptane, and the like. Two or more kinds of these solvents can be used in combination.

The amount of the solvent to be used is usually about 1 to 10 times the weight of the acetic acid ester [XI] (the total weight of the E and Z isomers).

The isomerization temperature is 0° to 100° C., preferably 20° to 80° C., and the reaction time is usually about 0.5 to 20 hours.

Also, according to the process in which the α-alkoxyiminophenylacetonitrile [VI] is hydrated to give the α-alkoxyiminophenylacetamide which is isomerized into the E isomer by treatment with an acid, followed by hydrolysis in the presence of a base, the acetic acid ester [XI] can be obtained at a higher E isomer ratio, and there is no need to effect the isomerization.

The (E)-α-alkoxyiminophenyl acetic acid ester [XI] obtained can be isolated by an ordinary method such as extraction, phase separation, water washing and concentration, if necessary. It may also be purified by a procedure such as column chromatography and recrystallization.

In the case where purification is attained by recrystallization, if the filtrate after the recrystallization is further subjected to recrystallization after the above-described isomerization, the (E)-α-alkoxyiminophenyl acetic acid ester [XI] can also be recovered from the filtrate after the recrystallization.

The acetyl halide [X] or the acetic acid ester [XI], which is the carboxylic acid derivative [VIII], can be converted into the N-alkyl-α-alkoxyiminophenylacetamide [IX] by reaction with an alkylamine.

As the alkylamine, lower alkylamines of the general formula: $R^4$-$NH_2$ are used. As the $R^4$, there can be mentioned, for example, $C_1$-$C_5$ alkyl such as methyl, ethyl, propyl, isopropyl, butyl, t-butyl and sec-butyl. As the typical examples of the alkylamine, there can be mentioned, for example, methylamine, ethylamine, propylamine, butylamine, and the like.

First, the following will describe the case where the acetyl halide [X] is reacted with an alkylamine.

The amount of the alkylamine to be used is 0.8 to 20 times, preferably 1 to 10 times, the moles of the acetyl halide [X].

The reaction is preferably effected in a mixed solvent consisting of an organic solvent and water. As the organic solvent to be used, there can be mentioned, for example, aromatic solvents such as benzene, toluene, xylene, chlorobenzene and o-dichlorobenzene; halogenated hydrocarbons such as dichloromethane, chloroform and 1,2-dichloroethane; aliphatic hydrocarbons such as hexane and heptane; ethers such as diisopropyl ether and methyl t-butyl ether, and the like. As the mixed solvent system consisting of such an organic solvent and water, there can be preferably mentioned aromatic solvent-water systems such as toluene-water system, and the like.

The amount of the solvent to be used is usually about 1 to 10 times the weight.

In the reaction, a base may be added, if necessary. As such a base, there can be mentioned, for example, hydroxides of alkali metals or alkaline earth metals, such as sodium hydroxide, potassium hydroxide and calcium hydroxide; carbonates of alkali metals, such as sodium carbonate and potassium carbonate; tertiary amines such as triethylamine, pyridine and diethyl aniline, and the like. Also, alkylamines as the reagent can also be used as the base. Two or more kinds of these bases can be used in combination.

The amount of the base to be used is usually 0.8 to 10 times, preferably 1 to 2 times, the moles of the acetyl halide [X]. In the case where this step is conducted without removing the acid halide forming agent in the previous step, an additional amount of the base should be added, which is corresponding to the residual acid halide forming agent in excess.

The reaction, although it is not particularly limited, is usually effected by adding dropwise a solution of the α-alkoxyiminophenylacetyl halide [X] to a mixture consisting of the alkylamine, organic solvent, water and base. To prevent hydrolysis of the α-alkoxyiminophenylacetyl halide [X], the reaction may also be effected while keeping the appropriate pH range, for example, pH 9 to 12, by simultaneously adding dropwise a solution of the α-alkoxyiminophenylacetyl halide [X] and base to a mixture consisting of the alkylamine, organic solvent and water.

The reaction temperature is usually 0° to 80° C., preferably 5° to 50° C., and the reaction time is usually about 0.5 to 20 hours.

The N-alkyl-α-alkoxyiminophenylacetamide [IX] formed can be isolated by subjecting the mixture solution to phase separation, removing the aqueous layer, and washing the organic layer with an acid such as diluted hydrochloric acid, followed by concentrating and bringing into dryness. If necessary, it can also be purified by recrystallization or the like.

Next, the following will describe the case where the acetic acid ester [XI] is reacted with an alkylamine.

The amount of the alkylamine to be used is 1 to 30 times, preferably 2 to 15 times, the moles of the acetic acid ester [XI].

The reaction is preferably effected in the presence of a solvent. As the solvent to be used, there can be mentioned, for example, aromatic solvents such as benzene, toluene, xylene, chlorobenzene and o-dichlorobenzene; aliphatic hydrocarbons such as hexane and heptane; $C_1$-$C_5$ alcohols such as methanol and ethanol; ethers such as diisopropyl ether and methyl t-butyl ether, and the like. Two or more kinds of these solvents can be used in combination.

The amount of the solvent to be used is usually 1 to 10 times the weight of the acetic acid ester [XI].

The reaction temperature is usually 0° to 100° C., preferably 10° to 40° C., and the reaction can be effected under normal or increased pressure.

The N-alkyl-α-alkoxyiminophenylacetamide [IX] formed can be isolated by concentrating the reaction mixture and bringing it into dryness.

If necessary, it may also be purified by recrystallization or the like.

The N-alkyl-α-alkoxyiminophenylacetamide [IX] thus obtained is usually obtained as a mixture of two isomers, i.e., E and Z isomers. As described above, the Z isomer can readily be isomerized into the E form by adding an acid to the solution obtained by the respective processes as described above.

As the specific examples of the N-alkyl-α-alkoxyiminophenylacetamide [IX], there can be mentioned, for example, N-methyl-α-methoxyimino-2-(phenoxymethyl)phenylacetamide, N-methyl-α-methoxyimino-2-(2-methylphenoxymethyl)phenylacetamide, N-methyl-α-methoxyimino-3-(2-methylphenoxymethyl)phenylacetamide, N-methyl-α-methoxyimino-4-(2-methylphenoxymethyl)phenylacetamide, N-methyl-α-methoxyimino-2-(3-methylphenoxymethyl)phenylacetamide, N-methyl-α-methoxyimino-2-(4-methylphenoxymethyl)phenylacetamide, N-methyl-α-methoxyimino-2-(2-ethylphenoxymethyl)phenylacetamide, N-methyl-α-methoxyimino-2-(2-propylphenoxymethyl)phenylacetamide, N-methyl-α-methoxyimino-2-(2-isopropylphenoxymethyl)phenylacetamide, N-methyl-α-methoxyimino-2-(2-sec-butylphenoxymethyl)phenylacetamide, N-methyl-α-methoxyimino-2-(4-tert-amylphenoxymethyl)phenylacetamide, N-methyl-α-methoxyimino-2-(2,3-dimethylphenoxymethyl)phenylacetamide, N-methyl-α-methoxyimino-2-(2,4-dimethylphenoxymethyl)phenylacetamide, N-methyl-α-methoxyimino-2-(2,5-dimethylphenoxymethyl)phenylacetamide, N-methyl-α-methoxyimino-2-(2,6-dimethylphenoxymethyl)phenylacetamide, N-methyl-α-methoxyimino-2-(3,4-dimethylphenoxymethyl)phenylacetamide, N-methyl-α-methoxyimino-2-(3,5-dimethylphenoxymethyl)phenylacetamide, N-methyl-α-methoxyimino-2-(2-methoxyphenoxymethyl)phenylacetamide, N-methyl-α-methoxyimino-2-(2-propenylphenoxymethyl)phenylacetamide, N-methylα-methoxyimino-2-(3-chloro-4-fluorophenoxymethyl)phenylacetamide, N-methyl-α-methoxyimino-2-(3-trifluoromethylphenoxymethyl)phenylacetamide, N-methyl-α-methoxyimino-2-(2-chloro-4-methylphenoxymethyl)phenylacetamide, N-methyl-α-methoxyimino-2-(2-chloro-5-methylphenoxymethyl)phenylacetamide, N-methyl-α-methoxyimino-2-(4-chloro-2-methylphenoxymethyl)phenylacetamide, N-methyl-α-methoxyimino-2-(4-chloro-3-methylphenoxymethyl)phenylacetamide, N-methyl-α-methoxyimino-2-(2,4-dichlorophenoxymethyl)phenylacetamide, N-ethyl-α-methoxyimino-2-(phenoxymethyl)phenylacetamide, N-ethyl-α-methoxyimino-2-(2-methylphenoxymethyl)phenylacetamide, N-ethyl-α-methoxyimino-2-(2,5-dimethylphenoxymethyl)phenylacetamide, N-ethyl-α-methoxyimino-2-(3-trifluoromethylphenoxymethyl)phenylacetamide, N-ethyl-α-methoxyimino-2-(4-chloro-2-methylphenoxymethyl)phenylacetamide, N-methyl-α-ethoxyimino-2-(phenoxymethyl)phenylacetamide, N-methyl-α-ethoxyimino-2-(2-methylphenoxymethyl)phenylacetamide, N-methyl-α-ethoxyimino-2-(2,5-dimethylphenoxymethyl)phenylacetamide, N-methyl-α-ethoxyimino-2-(3-trifluoromethylphenoxymethyl)phenylacetamide, N-methyl-α-ethoxyimino-2-(4-chloro-2-methylphenoxymethyl)phenylacetamide, N-ethyl-α-ethoxyimino-2-(phenoxymethyl)phenylacetamide, N-ethyl-α-ethoxyimino-2-(2-methylphenoxymethyl)phenylacetamide, N-ethyl-α-ethoxyimino-2-(2,5-dimethylphenoxymethyl)phenylacetamide, N-ethyl-α-ethoxyimino-2-(3-trifluoromethylphenoxymethyl)phenylacetamide, N-ethyl-α-ethoxyimino-2-(4-chloro-2-methylphenoxymethyl)phenylacetamide, and the like.

EXAMPLES

The present invention will be further illustrated by the following Examples, but it is needless to say that the present invention is not limited to these Examples.

Example 1-(1) Production of benzyl halide [III]

To 1619 g of toluene were added 788 g (4.50 mol) of α,α'-dichloro-o-xylene, 183 g (1.50 mol) of 2,5-dimethylphenol and 24.2 g (0.075 mol) of tetra-n-butylammonium bromide with stirring, to which 1246 g of water was added, and the mixture was heated to 60° C.

To this mixture was added dropwise 244 g (1.65 mol) of 27% aqueous sodium hydroxide solution over 5 hours, and the mixture was kept at the same temperature for 3 hours and then cooled to room temperature. The aqueous layer was removed by phase separation, and the organic layer was washed with 810 g of 5% hydrochloric acid and then washed twice with 810 g of water, after which α,α'-dichloro-o-xylene was removed by distillation to give 364 g of a mixture containing 279 g (1.07 mol, 71.3% yield) of 2-(2,5-dimethylphenoxymethyl)benzyl chloride and 57.7 g (0.167 mol, 22.2% yield) of 1,2-bis(2,5-dimethylphenoxymethyl)benzene. The mixture thus obtained can be used in the subsequent step after diluted by addition of toluene.

Example 1-(2)

To 140.0 g of toluene were added 113.8 g (0.65 mol) of α,α'-dichloro-o-xylene, 15.9 g (0.13 mol) of 2,5-dimethylphenol and 2.10 g (0.0065 mol) of tetra-n-butylammonium bromide with stirring, to which 108.0 g of water was added, and the mixture was heated to 60° C.

To this mixture was added dropwise 21.2 g (0.143 mol) of 27% aqueous sodium hydroxide solution over 5 hours, and the mixture was kept at the same temperature for 2 hours and then cooled to room temperature. The aqueous layer was removed by phase separation, and the organic layer was washed with 70.2 g of 5% hydrochloric acid and then washed twice with 70.2 g of water, after which α,α'-dichloro-o-xylene was removed by distillation to give 33.5 g of a mixture containing 26.4 g (0.101 mol, 77.8% yield) of 2-(2,5-dimethylphenoxymethyl)benzyl chloride and 3.08 g (0.0089 mol, 13.7% yield) of 1,2-bis(2,5-dimethylphenoxymethyl)benzene. The mixture thus obtained can be used in the subsequent step after diluted by addition of toluene.

Example 1-(3)

The reactions and post-treatment were conducted in the same manner as in Example 1-(2), except that 45.5 g (0.26 mol) of α,α'-dichloro-o-xylene was used, which afforded 36.7 g of a mixture containing 20.7 g (0.079 mol, 61.1% yield) of 2-(2,5-dimethylphenoxymethyl)benzyl chloride and 6.97 g (0.020 mol, 30.9% yield) of 1,2-bis-(2,5-dimethylphenoxymethyl)benzene.

Example 1-(4)

To 22.8 g (0.13 mol) of α,α'-dichloro-o-xylene, 15.9 g (0.13 mol) of 2,5-dimethylphenol and 2.10 g (0.0065 mol) of tetra-n-butylammonium bromide were added 140.3 g of toluene and then 108.0 g of water, followed by stirring. To this mixture was added dropwise 21.2 g (0.143 mol) of 27% aqueous sodium hydroxide solution at 60° C. over 5 hours, and the mixture was further kept at 60° C. for 9 hours. The reaction mixture was cooled to room temperature, and the aqueous layer was removed by phase separation. The organic layer was washed with 70.2 g of 5% hydrochloric acid and then washed twice with 70.2 g of water. The concentration of the organic layer gave 25.7 g of a mixture containing 12.1 g (0.0464 mol, 35.7% yield) of 2-(2,5-dimethylphenoxymethyl)benzyl chloride and 11.7 g (0.0338 mol, 52.0% yield) of 1,2-bis(2,5-dimethylphenoxymethyl)benzene.

Example 1-(5)

This Example was conducted in accordance with Example 1-(1), except that 214 g (1.50 mol) of 4-chloro-2-methylphenol was used instead of 183 g (1.50 mol) of 2,5-dimethylphenol and the temperature was kept at 60° C. for 3 hours in Example 1-(1). Thus, 381 g of a solution containing 2-(4-chloro-2-methylphenoxymethyl)benzyl chloride was obtained, which was analyzed by gas chromatography, and it was found that the content of 2-(4-chloro-2-methylphenoxymethyl)benzyl chloride was 72.0%. The yield of 2-(4-chloro-2-methylphenoxymethyl)benzyl chloride was 65.0% on the basis of 4-chloro- 2-methylphenol.

Example 2-(1) Production of phenylacetonitrile [IV]

A mixture comprising 266 g of water, 66.6 g (1.36 mol) of sodium cyanide, 16.4 g (0.051 mol) of tetra-n-butylammonium bromide and 439 g of toluene was heated to 80° C. with stirring, to which 715 g of a toluene solution of a mixture containing 266 g (1.02 mol) of 2-(2,5-dimethylphenoxymethyl)benzyl chloride and 56.5 g (0.163 mol) of 1,2-bis(2,5-dimethylphenoxymethyl)benzene, which had been produced in accordance with Example 1-(2), was added dropwise over 5 hours, and the mixture was further kept at the same temperature for 3 hours.

After cooling to room temperature, the aqueous layer was removed by phase separation, and the organic layer was washed three times with 379 g of 1% aqueous sodium hydroxide solution, and washed with 379 g of water and then with 379 g of 10% saline solution, which afforded 1141 g of the organic layer. To 716 g of this organic layer was added 43.3 g (0.064 mol) of 11% aqueous sodium hypochlorite solution, and the mixture was stirred at 23° C. for 3 hours, after which the precipitated insoluble materials were removed by filtration. The organic layer was washed with 100 g of 10% aqueous sodium sulfite solution, with 100 g of water and then with 10% saline solution, followed by concentration, which afforded 531.4 g of a mixture containing 157.1 g (0.625 mol, 97.7% yield) of 2-(2,5-dimethylphenoxymethyl)phenylacetonitrile and 35.4 g (0.102 mol, 99.5% recovery) of 1,2-bis(2,5-dimethylphenoxymethyl)benzene.

Example 2-(2)

In accordance with Example 1-(1), 372 g of a mixture containing 292 g (1.12 mol, 69.9% yield) of 2-(2,5-dimethylphenoxymethyl)benzyl chloride and 64.3 g (0.186 mol, 23.2% yield) of 1,2-bis(2,5-dimethylphenoxymethyl)benzene was obtained.

A mixture comprising 241 g of water, 60.2 g (1.23 mol) of sodium cyanide, 16.4 g (0.051 mol) of tetra-n-butylammonium bromide and 670 g of toluene was heated to 80° C. with stirring, to which a mixture obtained by adding 84.5 g of toluene to 338 g of the mixture produced above was added dropwise over 5 hours, and the mixture was further kept at the same temperature for 2.75 hours.

After cooling to room temperature, the aqueous layer was removed by phase separation, and the organic layer was washed with 345 g of 1% aqueous sodium hydroxide solution and washed twice with 345 g of water, followed by concentration, which afforded 306 g of a mixture containing 248 g (0.987 mol, 97.1% yield) of 2-(2,5 -dimethylphenoxymethyl)phenylacetonitrile and 57.5 g (0.166 mol, 98.3% recovery) of 1,2-bis(2,5-dimethylphenoxymethyl)benzene.

Example 2-(3)

A mixture comprising 196 g of water, 324 g of toluene, 49.0 g (1.00 mol) of sodium cyanide and 12.9 g (0.040 mol) of tetra-n-butylammonium bromide was heated to 80° C. with stirring, to which a mixture obtained by adding 313 g of toluene to 313 g of the solution produced in Example 1-(5) was added dropwise over 5 hours, and the mixture was further kept at the same temperature for 3 hours.

After cooling to room temperature, the aqueous layer was removed by phase separation, and the organic layer was washed three times with 338 g of 5% aqueous sodium hydroxide solution, and washed with 338 g of water and then with 338 g of 10% aqueous sodium chloride solution, followed by concentration, which afforded 725 g of a mixture containing 202 g (0.745 mol, 93.2% yield) of 2-(4-chloro-2-methylphenoxymethyl)phenylacetonitrile and 66.2 g (0.171 mol, 99.4% recovery) of 1,2-bis(4-chloro-2-methylphenoxymethyl)benzene.

Example 3-(1) Production of α-hydroxyiminophenylacetonitrile [V]

A mixture comprising 500 g of water, 434 g of toluene, 103.5 g (1.50 mol) of sodium nitrite and 113.4 g (1.53 mol) of 1-butanol was cooled to 0° C. with stirring, to which 156.3 g (1.50 mol) of 35% hydrochloric acid was added dropwise over 5 hours, and the mixture was further kept at the same temperature for 2 hours. This mixture was subjected to phase separation, and the organic layer was washed twice with 250 g of 4% sodium hydrogen carbonate and further washed with 250 g of 20% saline solution.

The toluene solution of butyl nitrite thus obtained was analyzed by gas chromatography with an internal standard method. As a result, the content of butyl nitrite was 26.1% and the yield was 98.7% on the basis of sodium nitrite.

To 527.2 g of a toluene solution of a mixture containing 155.8 g (0.620 mol) of 2-(2,5-dimethylphenoxymethyl)phenylacetonitrile and 35.1 g (0.101 mol) of 1,2-bis( 2,5-dimethylphenoxymethyl)benzene, which had been obtained in accordance with Example 2-(1), were added 50.3 g (0.896 mol) of potassium hydroxide and 125.7 g of n-butanol with stirring at 22°–25° C., to which 308.3 g of a toluene solution containing 79.2 g (0.768 mol) of butyl nitrite produced in accordance with the foregoing was added dropwise at the stone temperature over 5 hours, and the mixture was further kept at the same temperature for 2 hours.

To this reaction mixture was added 620 g of water, and the mixture was heated to 60° C. and further kept at the same temperature for 3 hours. This mixture was heated under reduced pressure, and toluene and n-butanol were removed by distillation while adding water, if necessary, followed by two washings with 300 g of toluene.

Thus, 1262.7 g of an aqueous solution containing 189.1 g (0.594 mol, 95.8% yield, E/Z=15/85) of the potassium salt of α-hydroxyimino-2-(2,5-dimethylphenoxymethyl)phenylacetonitrile was obtained. It was found that 1,2-bis(2,5-dimethylphenoxymethyl)benzene was not found in the aqueous solution, but contained at an amount of 33.7 g (0.097 mol, 96.1% recovery) in 594 g of toluene after washing.

Example 3-(2)

To 50.42 g of toluene were added 29.77 g of the mixture obtained in Example 2-(2), 6.46 g of methanol and 6.46 g (115 mmol) of potassium hydroxide with stirring at room temperature, to which 11.87 g (115 mmol) of commercially available butyl nitrite was added dropwise at the same temperature over 2 hours, and the mixture was further stirred at the same temperature for 3 hours. Then, 104 g of the homogeneous solution obtained was divided into two portions.

To 52 g of one of the two-divided solutions was added 50 g of water, followed by extraction and phase separation, and the aqueous layer obtained was washed twice with 25 ml of toluene, cooled to 15° C. and adjusted to pH 1 by use of 36% hydrochloric acid. Then, 50 ml of diethyl ether was added for extraction, followed by phase separation, and the aqueous layer was further extracted twice with 25 ml of diethyl ether. All the ether layers obtained were combined together, and these layers were washed three times with 30 ml of 10% saline solution, dried with anhydrous sodium sulfate and concentrated, which afforded 13.65 g of a pale pink solid.

The analysis by high performance liquid chromatography revealed that the content of α-hydroxyimino-2-(2,5-dimethylphenoxymethyl)phenylacetonitrile was 95.1% (96.5% yield, E/Z=20/80), but 1,2-bis(2,5-dimethylphenoxymethyl)benzene was not contained.

Example 3-(3)

First, 52 g of the other of the two-divided solution in Example 3-(2) was cooled to 15° C. and adjusted to pH 1 by use of 36% hydrochloric acid, to which 50 ml of diethyl ether and 25 ml of water were added, followed by extraction and phase separation. The aqueous layer was further extracted twice with 25 ml of diethyl ether, and all the separated ether layers were combined together, washed three times with 30 ml of 10% saline solution, dried with anhydrous sodium sulfate and concentrated, which afforded 17.65 g of a brown solid.

The content of α-hydroxyimino-2-(2,5-dimethylphenoxymethyl)phenylacetonitrile was 74.5% (97.7% yield, E/Z=20/80).

The content of 1,2-bis(2,5-dimethylphenoxymethyl)benzene was 15%.

Example 3-(4)

To 264.5 g of a toluene solution of a mixture containing 75.40 g (300 mmol) of 2-(2,5-dimethylphenoxymethyl)phenylacetonitrile and 17.54 g (50.6 mmol) of 1,2-bis-( 2,5-dimethylphenoxymethyl)benzene, which had been obtained in accordance with Example 2-(2), were added 23.57 g (420 mmol) of potassium hydroxide and 58.93 g of n-butanol with stirring at room temperature, to which 142.1 g of a toluene solution containing 37.12 g (360 mmol) of butyl nitrite produced in accordance with Example 3-(1) was added dropwise at the same temperature over 5 hours, and the mixture was further kept at the same temperature for 2.8 hours.

To 486.9 g of the homogeneous solution obtained was added 298 g of water, and the mixture was heated to 50° C. and further kept at the same temperature for 3 hours. This mixture was heated under reduced pressure, and toluene and n-butanol were removed by distillation while adding water, if necessary, to yield 635 g, followed by two washings with 150 g of toluene.

Thus, 624.9 g of an aqueous solution containing 91.15 g (286 mmol, 95.4% yield, E/Z=18/82) of the potassium salt of α-hydroxyimino-2-(2,5-dimethylphenoxymethyl)phenylacetonitrile was obtained, which was neutralized with 36% hydrochloric acid. It was found that 1,2-bis(2,5-dimethylphenoxymethyl)benzene was not found in the aqueous solution, but contained at an amount of 17.43 g (50.3 mmol, 99.4% recovery) in 299 g of the toluene layer after washing.

Example 3-(5)

To 676.1 g of a toluene solution of a mixture containing 188.9 g (695 mmol) of 2-(4-chloro-2-methylphenoxymethyl)phenylacetonitrile and 61.8 g ( 160 mmol) of 1,2-bis(4-chloro-2-methylphenoxymethyl)benzene, which had been produced in Example 2-(3), were added 56.8 g (978 mmol) of potassium hydroxide and 142 g of n-butanol with stirring at room temperature, to which 86.47 g (839 mmol) of butyl nitrite was added dropwise at the same temperature over 5 hours, and the mixture was further kept at the same temperature for 3 hours.

To 961 g of the homogeneous solution obtained was added 588 g of water, and the mixture was heated under reduced pressure, and toluene and n-butanol were removed by distillation while adding water, if necessary, to yield 1271 g, followed by two washings with 350 g of toluene.

Thus, 1288 g of an aqueous solution containing 239.7 g (707 mmol, 102% yield) of the potassium salt of α-hydroxyimino-2-(4-chloro-2-methylphenoxymethyl)phenylacetonitrile was obtained, which was neutralized with 36% hydrochloric acid. It was found that 1,2-bis(4-chloro-2-methylphenoxymethyl)benzene was not found in the aqueous solution, but contained at an amount of 61.8 g (160 mmol, 100% recovery) in 683 g of the toluene layer after washing.

Example 4-(1) Production of α-alkoxyiminophenylacetonitrile [VI]

To a mixture of 977 g of toluene and 9.44 g (0.029 mol) of tetra-n-butylammonium bromide were simultaneously added dropwise 84.3 g (0.668 mol) of dimethyl sulfate and 1267.6 g of an aqueous solution containing 177.2 g (0.557 mol, E/Z=15/85) of the potassium salt of α-hydroxyimino-2-(2,5-dimethylphenoxymethyl)phenylacetonitrile produced in accordance with Example 3-(1) over 4.8 hours while keeping at 23°–25° C., and the reaction was subsequently allowed to proceed at the same temperature for 2.5 hours. The aqueous layer was removed from the reaction mixture by phase separation, and the organic layer was washed with 489 g of 5% aqueous sodium hydroxide solution and then with 176 g of 10% saline solution, which afforded 1182.7 g of a toluene solution containing α-methoxyimino-2-(2,5-dimethylphenoxymethyl)phenylacetonitrile. (The hue in 5-fold dilution was No. 16 on the Gardner scale.)

To 1162.7 g of the toluene solution was added dropwise 37.0 g (0.055 mol) of 11% aqueous sodium hypochlorite solution at 26° C., and the stirring was continued at the same temperature for 3 hours. To the reaction mixture was added 138 g of 5% aqueous sodium sulfite solution, and the organic layer was washed with 400 g of 5% saline solution and then with 200 g of 10% saline solution, after which the slightly precipitated solid was removed by filtration. The filtrate was allowed to stand and subjected to phase separation to remove the aqueous layer, and the organic layer was concentrated, which afforded a 1169.9 g of a toluene solution containing α-methoxyimino-2-(2,5 -dimethylphenoxymethyl)phenylacetonitrile. (The hue in 5-fold dilution was No. 10 on the Gardner scale.)

The toluene solution obtained was analyzed by high performance liquid column chromatography, and it was found that the yield of α-methoxyimino-2-(2,5-dimethylphenoxymethyl)phenylacetonitrile was 98.5% (E/Z=17/83).

Example 4-(2)

To a mixture of 1184 g of toluene and 17.3 g (0.054 mol) of tetra-n-butylammonium bromide were simultaneously added dropwise 163 g (1.29 mol) of dimethyl sulfate and 1866 g of an aqueous solution containing 344 g (1.08 mol, E/Z=16/84) of the potassium salt of α-hydroxyimino-2-(2, 5-dimethylphenoxymethyl)phenylacetonitrile produced in accordance with Example 3-(2) over 5 hours while keeping at 20°–25° C., and the reaction was subsequently allowed to proceed at the same temperature for 1 hour. The aqueous layer was removed from the reaction mixture by phase separation, and the organic layer was washed with 5% aqueous sodium hydroxide solution and then washed twice with 296 g of 10% saline solution, which afforded 1841 g of a toluene solution containing α-methoxyimino-2-(2,5-dimethylphenoxymethyl)phenylacetonitrile. The toluene solution obtained was analyzed by high performance liquid chromatography, and it was found that the yield of α-methoxyimino-2-(2,5-dimethylphenoxymethyl)phenylacetonitrile was 91.6% (E/Z=18/82) and the yield of the nitron compound as a by-product was 5.7% (E/Z=91/9).

Example 4-(3)

To a mixture of 924 g of toluene and 13.6 g (0.042 mol) of tetra-n-butylammonium bromide were simultaneously added dropwise 127 g (1.01 mol) of dimethyl sulfate and 1460 g of an aqueous solution containing 268 g (0.84 mol, E/Z=19/81) of the potassium salt of α-hydroxyimino-2-(2, 5-dimethylphenoxymethyl)phenylacetonitrile produced in accordance with Example 3-(2) over 5 hours while keeping at 20°–25° C., and the reaction was subsequently allowed to proceed at the same temperature for 1.5 hours. The aqueous layer was removed from the reaction mixture by phase separation, and the organic layer was washed with 1000 g of 5% aqueous sodium hydroxide solution and then washed twice with 250 g of 10% saline solution. The organic layer was concentrated under reduced pressure and dried, which afforded 245 g of α-methoxyimino-2-( 2,5-dimethylphenoxymethyl)phenylacetonitrile. The analysis by high performance liquid chromatography revealed that the content and yield of α-methoxyimino-2-(2,5-dimethylphenoxymethyl)phenylacetonitrile was 89.6% and 88.6% (E/Z=17/83), respectively, and the content and yield of the nitron compound as a by-product was 4.8% and 4.7% yield (E/Z=91/9), respectively.

Example 4-(4)

To a mixture of 17 g of toluene, 20 g of water, 1.39 g (24.0 mmol) of potassium hydroxide, 5.94 g (20.0 mmol, E/Z= 20/80) of α-hydroxyimino-2-(2,5-dimethylphenoxymethyl)phenylacetonitrile produced in accordance with Example 3-(2) and 0.32 g (1.00 mmol) of tetra-n-butylammonium bromide was added dropwise 3.03 g (24.0 mmol) of dimethyl sulfate over 5 hours while keeping at 20°–25° C., and the mixture was subsequently kept at the same temperature for 1 hour to effect the reaction. The aqueous layer was removed from the reaction mixture by phase separation, and the organic layer was washed twice with water and concentrated, which afforded 6.17 g of a solid containing α-methoxyimino-2-(2,5-dimethylphenoxymethyl)phenylacetonitrile. The analysis by high performance liquid chromatography revealed that the yield of α-methoxyimino-2-(2,5-dimethylphenoxymethyl)phenylacetonitrile was 81.3% (E/Z=8/92) and the yield of the nitron compound as a by-product was 15.6% (E/Z=81/19).

Example 4-(5)

To a mixture of 17 g of toluene, 20 g of water, 1.39 g (24.0 mmol) of potassium hydroxide and 5.94 g (20.0 mmol, E/Z=20/80) of α-hydroxyimino-2-(2,5 -dimethylphenoxymethyl)phenylacetonitrile produced in accordance with Example 3-(2) was added dropwise 3.03 g (24.0 mmol) of dimethyl sulfate over 5 hours while keeping at 20°–25° C., and the mixture was subsequently kept at the same temperature for 1 hour to effect the reaction. The aqueous layer was removed from the reaction mixture by phase separation, and the organic layer was washed twice with water and concentrated, which afforded 6.08 g of a solid containing α-methoxyimino-2-(2,5-dimethylphenoxymethyl)phenylacetonitrile. The analysis by high performance liquid chromatography revealed that the yield of α-methoxyimino-2-(2,5-dimethylphenoxymethyl)phenylacetonitrile was 71.7% (E/Z=6/94) and the yield of the nitron compound as a by-product was 23.9% (E/Z=64/36).

Example 4-(6)

To a mixture of 101 g of toluene and 0.91 g (2.8 mmol) of tetra-n-butylammonium bromide were simultaneously added dropwise 8.57 g (67.9 mmol) of dimethyl sulfate and 111 g of an aqueous solution containing 17.7 g (52.3 mmol) of the potassium salt of α-hydroxyimino-2-(4-chloro-2-methylphenoxymethyl)phenylacetonitrile produced in accordance with Example 3-(5) over 3 hours while keeping at 20°–25° C., and the reaction was subsequently allowed to proceed at the same temperature for 2 hours. The aqueous layer was removed from the reaction mixture by phase separation, and the organic layer was washed with 47 g of 5% aqueous sodium hydroxide solution and then washed twice with 47 g of 10% saline solution, which afforded 249 g of a toluene solution containing α-methoxyimino-2-(4-chloro-2-methylphenoxymethyl)phenylacetonitrile. The toluene solution obtained was analyzed by high performance liquid chromatography, and it was found that the yield of α-methoxyimino-2-(4-chloro-2 -methylphenoxymethyl)phenylacetonitrile was 98.5%.

Example 4-(7)

First, 1720 g of a toluene solution containing 116 g (367 mmol, E/Z= 21.4/78.6) of α-methoxyimino-2-(4-chloro-2-methylphenoxymethyl)phenylacetonitrile produced in accordance with Example 4-(6) was subjected to solvent removal, followed by drying under reduced pressure, which afforded 123 g of a brown powder. To this powder was added 262 g of toluene for dissolution, and recrystallization gave 77.2 g of a white powder (66.8% recovery). This powder was analyzed by high performance liquid chromatography, and it was found that the purity of α-methoxyimino-2-(4-chloro-2-methylphenoxymethyl)phenylacetonitrile was 99.7% (E/Z=0.3/99.7).

The mother liquid of crystallization was concentrated and dried to give 45.53 g of a viscous solid. To 20 g (84.6% purity, E/Z=63.5/36.5) of this solid were added 48.2 g of toluene and 27.2 g (267 mmol) of 36% hydrochloric acid, followed by heating to 80° C., and the reaction was allowed to proceed at the same temperature for 23 hours. To the reaction mixture obtained was added 30 g of water, and the aqueous layer was removed by phase separation. Two washings with 30 g of water were conducted, and the solvent was removed by distillation under reduced pressure until the total weight became 56.4 g. This residue was analyzed by high performance liquid chromatography, and it was found that the E/Z ratio was changed to 29.0/71.0. This residue was recrystallized to give 8.33 g of a white powder of α-methoxyimino-2-(4-chloro- 2-methylphenoxymethyl)phenylacetonitrile (16.3% recovery). This powder was analyzed by high performance liquid chromatography, and it was found that the purity of α-methoxyimino-2-(4-chloro-2-methylphenoxymethyl)phenylacetonitrile was 96.6% (E/Z =0.8/99.2).

Example 5-(1) Production of α-alkoxyiminophenylacetic acid [VII]

To a mixture of 107 g of methanol and 459 g of a toluene solution containing 152.9 g (0.519 mol, E/Z=17/83) of α-methoxyimino-2-(2,5-dimethylphenoxymethyl)phenylacetonitrile produced in accordance with Example 4-(1) was added dropwise 130 g of an aqueous solution containing 58.5 g, (1.04 mol) of potassium hydroxide over 2 hours while keeping at 70°–73° C., and the reaction was subsequently allowed to proceed at 73° C. for 30 hours.

To the reaction mixture was added 452 g of water, and while adding dropwise 700 g of water, methanol was removed by distillation to give 797.9 g of an aqueous solution containing potassium α-methoxyimino-2-(2,5-dimethylphenoxymethyl)phenylacetate. To 784.1 g of this aqueous solution was added 109 g of toluene, and the organic layer was removed by phase separation at 60°–65° C., which afforded 735 g of an aqueous solution containing potassium α-methoxyimino-2-(2,5-dimethylphenoxymethyl)phenylacetate.

To a mixture of this aqueous solution and 300 g of toluene was added dropwise 106 g (1.05 mol) of 36% hydrochloric acid over 5 hours while keeping at 50°–55° C., so that the pH was adjusted to 2–2.2. The aqueous layer was removed from the reaction mixture by phase separation at 50°–55° C. The organic layer was washed twice with 191 g of water, followed by azeotropic removal of water, which afforded 552.8 g of a toluene solution containing α-methoxyimino-2-(2,5-dimethylphenoxymethyl)phenylacetic acid.

The toluene solution obtained was analyzed by high performance liquid chromatography, and it was found that the yield of α-methoxyimino-2-(2,5-dimethylphenoxymethyl)phenylacetic acid was 96.4% (E/Z=23/77).

Example 5-(2) Production of α-alkoxyiminophenylacetic acid [VII]

To a mixture of 49 g of methanol, 70.0 g (0.222 mol, E/Z=0.3/99.7) of α-methoxyimino-2-(4-chloro-2-methylphenoxymethyl)phenylacetonitrile in 99.7% purity and 140 g of toluene was added dropwise 55.5 g of an aqueous solution containing 25.0 g (0.446 mol) of potassium hydroxide over 2 hours while keeping at 70°–73° C., and the reaction was subsequently allowed to proceed at 73° C. for 28 hours.

The reaction mixture was concentrated and dried under reduced pressure to give 106.88 g of a white solid containing potassium α-methoxyimino-2-(4-chloro-2-methylphenoxymethyl)phenylacetate. To this solid were added 250 g of water and 46 g of toluene, and the organic layer was removed by phase separation at 60°–65° C. The aqueous layer was washed with 46 g of toluene, which afforded an aqueous solution containing potassium α-methoxyimino-2-(4-chloro-2-methylphenoxymethyl)phenylacetate.

To a mixture of this solution and 290 g of toluene was added dropwise 45.0 g (0.444 mol) of 36% hydrochloric acid over 5 hours while keeping at 50°–55° C., so that the pH was adjusted to 2–2.2. The aqueous layer was removed from the reaction mixture by phase separation at 50°–55° C. The organic layer was washed twice with 85 g of water, and the solvent was removed by distillation under reduced pressure, which afforded 72.38 g of a white solid containing α-methoxyimino-2-(4-chloro-2-methylphenoxymethyl)phenylacetic acid.

The white solid was analyzed in the form of a toluene solution by high performance liquid chromatography, and it was found that the yield of α-methoxyimino- 2-(4-chloro-2-methylphenoxymethyl)phenylacetic acid was 93.6% (E/Z=3.5/96.5).

Example 6-(1) Production of α-alkoxyiminophenylacetyl halide [X]

Into 629 g of a toluene solution containing 144.7 g (0.462 mol, E/Z=25/75) of α-methoxyimino-2-(2,5-dimethylphenoxymethyl)phenylacetic acid produced in accordance with Example 5-(1) and 0.338 g (0.0046 mol) of dimethylformamide was introduced 68.5 g (0.692 mol) of phosgene over 10 hours while keeping at 60°–65° C., and the reaction was subsequently allowed to proceed at the same temperature for 2 hours and then at 80° C. for 2 hours. Then, excess phosgene was removed by distillation, followed by dilution with toluene, which afforded 612.6 g of a toluene solution of α-methoxyimino- 2-(2,5-dimethylphenoxymethyl)phenylacetyl chloride.

In this reaction, an isomerization reaction from Z form to E form proceeded at the same time, so that the E/Z ratio was changed from 25/75 before the reaction to 94/6 after the reaction.

Example 6-(2) Production of α-alkoxyiminophenylacetyl halide [X]

To 232 g of a toluene solution containing 50.1 g (0.160 mol, E/Z=23/77) of α-methoxyimino-2-(2,5-dimethylphenoxymethyl)phenylacetic acid produced in accordance with Example 5-(1) and 0.117 g (0.0016 mol) of dimethylformamide was added dropwise a mixed solution of 23.8 g (0.240 mol) of phosgene and 45.1 g of toluene over 5 hours while keeping at 60°–65° C., and the reaction was subsequently allowed to proceed at the same temperature for 5 hours, which afforded 239.0 g of a toluene solution of α-methoxyimino-2-(2,5-dimethylphenoxymethyl)phenylacetyl chloride.

Example 6-(3)

To a mixture of 8.23 g of toluene and 0.132 g (1.81 mmol) of dimethylformamide were simultaneously added dropwise 33.3 g of a toluene solution containing 9.40 g (30.0 mmol, E/Z=22/78) of α-methoxyimino-2-(2,5-dimethylphenoxymethyl) phenylacetic acid produced in accordance with Example 5-(1) and 4.64 g (39.0 mmol) of thionyl chloride over 5 hours while keeping at 60°–65° C., and the reaction was subsequently allowed to proceed at the same temperature for 2 hours, which afforded 43.3 g of a toluene solution containing α-methoxyimino-2-(2,5-dimethylphenoxymethyl)phenylacetyl chloride.

Example 6-(4) Production of α-alkoxyiminophenylacetyl halide [X]

To 32.5 g of a toluene solution containing 9.40 g (30.0 mmol, E/Z=22/78) of α-methoxyimino-2-(2,5-dimethylphenoxymethyl)phenylacetic acid produced in accordance with Example 5-(1) and 0.132 g (1.8 mmol) of dimethylformamide was added dropwise 4.64 g (39.0 mmol) of thionyl chloride over 5 hours while keeping at 60°–65° C., and the reaction was subsequently allowed to proceed at the same temperature for 2 hours, which afforded 34.1 g of a toluene solution of α-methoxyimino-2-(2,5-dimethylphenoxymethyl)phenylacetyl chloride.

Example 6-(5) Production of α-alkoxyiminophenylacetyl halide [X]

To a mixture of 52.24 g (0.150 mol, E/Z=3.5/96.5) of α-methoxyimino-2-( 4-chloro-2-methylphenoxymethyl)phenylacetic acid produced in accordance with Example 5-(2), 0.57 g (0.0078 mol) of dimethylformamide and 203 g of toluene was added dropwise 25.9 g (0.204 mol) of oxalyl chloride over 3 hours while keeping at 60°–65° C., and the reaction was subsequently allowed to proceed at the same temperature for 1 hours and then 80° C. for 2 hours, which afforded 265 g of a toluene solution of α-methoxyimino-2-(4-chloro-2-methylphenoxymethyl)phenylacetyl chloride.

In this reaction, an isomerization reaction from Z form to E form proceeded at the same time, so that the E/Z ratio was changed from 3.5/96.5 before the reaction to 83/17 after the reaction.

Example 7-(1) Production of α-alkoxyiminophenyl acetate [XI]

A mixture of 193 g of an aqueous solution containing 35.1 g (0.100 mol, E/Z =14/86) of the potassium salt of α-methoxyimino-2-(2,5-dimethylphenoxymethyl)phenylacetic acid produced in accordance with Example 5-(1), 92.7 g of toluene and 21 g of methanol was adjusted to pH 6.4 by addition of 36% hydrochloric acid, to which 1.61 g of tetra-n-butylammonium bromide was added and then 23.3 g (0.185 mol) of dimethyl sulfate was added dropwise at 48°–52° C. over 2 hours while adjusting to pH 6–6.5 by addition of 45% aqueous potassium hydroxide solution, and the reaction was subsequently allowed to proceed at the same temperature for 2 hours. The reaction mixture was adjusted to pH 10 by addition of 45% aqueous potassium hydroxide solution, and kept at the same temperature for 1 hour. The aqueous layer was removed by phase separation. The organic layer was washed twice with 50 g of water, and the solvent was removed by distillation under reduced pressure, which afforded 37.6 g of a brown solid containing methyl α-methoxyimino-2-(2,5-dimethylphenoxymethyl)phenylacetate.

This solid was analyzed by high performance liquid chromatography, and it was found that the content of methyl α-methoxyimino-2-(2,5-dimethylphenoxymethyl) phenylacetate was 32.2 g (0.0983 mol, 98.3% yield, E/Z=14/86).

To a mixture of 1.00 g of a brown solid containing 0.895 g (2.73 mmol, E/Z =14/86) of methyl α-methoxyimino-2-(2,5-dimethylphenoxymethyl)phenylacetate obtained in accordance with the above method and 3.00 g of toluene was added 1.38 g (13.7 mmol) of 36% hydrochloric acid at 60° C., and the reaction was subsequently allowed to proceed at the same temperature for 10 hours.

This mixture was analyzed by high performance liquid chromatography, and it was found that the reaction proceeded quantitatively and the E/Z ratio was changed to 84/16.

Example 7-(2)

First, 50 g of toluene, 10.5 g (328 mmol) of methanol and 8.62 g (109 mmol) of pyridine were mixed and cooled to 5°–10° C., and the reaction was allowed to proceed at the same temperature for 2 hours, followed by allowing to stand at room temperature overnight. The reaction mixture was cooled to 0°–10° C., to which a toluene solution containing α-methoxyimino-2-(2,5-dimethylphenoxymethyl)phenylacetyl chloride produced in accordance with Example 6-(2) was added dropwise at the same temperature over 0.5 hours. Further, 50 ml of water was added dropwise at the same temperature, and the pH was adjusted to 1.5–2.0 by addition of 36% hydrochloric acid at the same temperature. To this mixture was added 100 ml of toluene, followed by extraction and phase separation. The organic layer was washed with 50 ml of water and then with 50 ml of 5% aqueous sodium hydrogen carbonate solution, and subsequently washed twice with 50 ml of 10% saline solution, followed by concentration, which afforded 65.2 g of a toluene solution containing methyl α-methoxyimino-2-(2,5-dimethylphenoxymethyl)phenylacetate.

The toluene solution obtained was analyzed by high performance liquid chromatography, and it was found that the content of methyl α-methoxyimino-2-(2,5-dimethylphenoxymethyl)phenylacetate was 8.93 g (27.3 mmol, 83.1% yield on the basis of α-methoxyimino-2-(2,5-dimethylphenoxymethyl)phenylacetic acid, E/Z=95/5).

Example 7-(3)

A toluene solution of α-methoxyimino-2-(2,5-dimethylphenoxymethyl)phenylacetic acid produced in accordance with Example 5-(1) was concentrated and brought into dryness, which afforded 37.4 g of a solid containing 30.0 g (95.7 mmol, E/Z=23/77) of α-methoxyimino-2-(2,5-dimethylphenoxymethyl)phenylacetic acid. This solid was dissolved in 150 g of methanol, and 11.0 g (302 mmol) of hydrogen chloride gas was introduced into the solution while keeping at 0°–15° C., followed by heating to 30° C. and stirring at 30° C. for 20 hours. To this solution was added 38 g of toluene at the same temperature. Subsequently, the mixture was stirred at the same temperature for 4 hours and then heated to 40° C., and the stirring was continued for 5 hours. After completion of the reaction, the reaction mixture was concentrated, and 270 g of toluene and 270 g of 3% aqueous sodium hydroxide solution were added to the residue, followed by extraction and phase separation to remove the aqueous layer. The organic layer was further washed with 3% aqueous sodium hydroxide solution to give 304.9 g of the organic layer.

This organic layer was analyzed by high performance liquid chromatography, and it was found that methyl α-methoxyimino-2-(2,5-dimethylphenoxymethyl)phenylacetate was contained at an amount of 31.1 g (95.1 mmol, 99.4% yield, E/Z=76/24).

Example 7-(4)

To a mixture of 30.4 g of methanol and 137 g of a toluene solution containing 43.5 g (0.148 mol, E/Z=10/90) of α-methoxyimino-2-(2,5-dimethylphenoxymethyl)phenylacetonitrile produced in accordance with Example 4-(1) was added 10.3 g (0.177 mol) of 96.7% potassium hydroxide, and the mixture was heated under reflux for 4 hours. The reaction mixture was cooled to 0°–5° C., to which 50 g of water was added, and the pH was adjusted to 2 by addition of 36% hydrochloric acid. To this mixture was added 87 g of toluene, and the mixture was heated to 60°–65° C., after which the aqueous layer was removed by phase separation. The organic layer was washed twice with 50 g of water, and the solvent was removed by distillation under reduced pressure, which afforded 57.0 g of a brown solid containing α-methoxyimino-2-(2,5-dimethylphenoxymethyl)phenylacetamide.

To a mixture of 56.9 g of this brown solid and 224 g of toluene was added 14.9 g (0.148 mol) of 36% hydrochloric acid at 60° C., and the reaction was subsequently allowed to proceed at the same temperature for 3 hours. To the reaction mixture was added 100 g of water, and the aqueous layer was removed by phase separation. The organic layer was washed twice with 100 g of water, and the solvent was removed by distillation under reduced pressure, which afforded 51.1 g of a brown solid containing (E)-α-methoxyimino-2-(2,5-dimethylphenoxymethyl)phenylacetamide.

To a mixture of 20.0 g of this brown solid, 34.0 g of toluene and 11.9 g of methanol was added dropwise 14.4 g (0.116 mol) of 45% aqueous potassium hydroxide solution at 70°–73° C. over 1 hour, and the reaction was subsequently allowed to proceed at 73° C. for 12 hours. From the reaction mixture, toluene was removed by distillation, and water was added, which afforded 100 g of an aqueous solution containing the potassium salt of (E)-α-methoxyimino-2-(2,5-dimethylphenoxymethyl)phenylacetic acid.

To a mixture obtained by adding 56.7 g of toluene and tetra-n-butylammonium bromide to this solution was added 36% hydrochloric acid to adjust the pH to 6.4. To this mixture was added dropwise 13.5 g (0.107 mol) of dimethyl sulfate at 48°–52° C. over 1 hour while controlling the pH to 6–6.5 by addition of 45% aqueous potassium hydroxide solution, and the reaction was subsequently allowed to proceed at the same temperature for 1 hour. To the reaction mixture was added 45% aqueous potassium hydroxide solution to adjust the pH to 10, and the mixture was kept at the same temperature for 1 hour, after which the aqueous layer was removed by phase separation. The organic layer was washed twice with 40 g of water, and the solvent was removed by distillation under reduced pressure, which afforded 20.6 g of a brown solid containing methyl α-methoxyimino-2-(2,5-dimethylphenoxymethyl)phenylacetate.

This solid was analyzed by high performance liquid chromatography, and it was found that methyl α-methoxyimino-2-(2,5-dimethylphenoxymethyl)phenylacetate was contained at an amount of 17.4 g (0.0530 mol, 91.7% yield on the basis of α-methoxyimino- 2-(2,5-dimethylphenoxymethyl)phenylacetonitrile), E/Z=94/6).

Reference Example 1-(1) Production of N-alkyl-α-alkoxyiminophenylacetamide [IX]

To a mixture of 69.8 g of water, 43.0 g (0.554 mol) of 40% aqueous methylamine solution and 124.6 g of toluene were simultaneously added dropwise 612.6 g of a toluene solution containing α-methoxyimino-2-(2,5-dimethylphenoxymethyl)phenylacetyl chloride obtained in Example 6-(1) and 80.3 g (0.462 mol) of 23% aqueous sodium hydroxide solution at 20°–25° C. over 6 hours while controlling the pH to 10 or higher, and the reaction was subsequently allowed to proceed at the same temperature for 1 hour. The reaction mixture was heated to 65° C., after which the aqueous layer was removed by phase separation. The organic layer was washed with 170 g of 1N hydrochloric acid and then further washed twice with 170 g of water, which afforded 711.0 g of a toluene solution containing N-methyl-α-methoxyimino-2-(2,5-dimethylphenoxymethyl)phenylacetamide.

Then, 50.0 g of this solution was concentrated and brought into dryness, which afforded 11.6 g of a yellowish brown solid. This solid was analyzed by high performance liquid chromatography, and it was found that N-methyl-α-methoxyimino-2-( 2,5-dimethylphenoxymethyl)phenylacetamide was contained at an amount of 10.27 g (0.0316 mol, the yield on the basis of α-methoxyimino-2-(2,5-dimethylphenoxymethyl)phenylacetic acid was 97.0%, E/Z=94/6).

Then, 11.62 g of this solid was recrystallized from toluene to give 8.22 g of yellowish white crystals. These crystals were analyzed by high performance liquid chromatography, and it was found that the purity of N-methyl-α-methoxyimino-2-(2,5-dimethylphenoxymethyl)phenylacetamide was 99.4% (E/Z=99/1). No by-product was found.

Reference Example 1-(2)

A toluene solution containing α-methoxyimino-2-(2,5-dimethylphenoxymethyl)phenylacetyl chloride produced in accordance with Example 6-(2) was added dropwise to a mixture of 300 g of toluene, 124 g (1.60 mol) of 40% aqueous methylamine solution and 150 g of water at 10°–20° C. over 1 hour, and the reaction was allowed to proceed at the same temperature for 1 hour. The reaction mixture was heated to 60° C., after which the aqueous layer was removed by phase separation. The organic layer was washed with 200 g of 1N HCl and then washed twice with 200 g of water, after which the organic layer was concentrated and brought into dryness, which afforded 57.1 g of a yellowish brown solid.

This solid was analyzed by high performance liquid chromatography, and it was found that N-methyl-α-methoxyimino-2-(2,5-dimethylphenoxymethyl)phenylacetamide was contained at an amount of 50.3 g (0.154 mol, the yield on the basis of α-methoxyimino- 2-(2,5-dimethylphenoxymethyl)phenylacetic acid was 96.3%, E/Z=94/6). Further, no by-product was found.

Reference Example 1-(3)

A toluene solution containing α-methoxyimino-2-(2,5-dimethylphenoxymethyl)phenylacetyl chloride produced in accordance with Example 6-(3) was added dropwise to a mixture of 100 g of toluene, 24.8 g (320 mmol) of 40% aqueous methylamine solution and 50 g of water at 10°–20° C. over 0.5 hours, and the reaction was allowed to proceed at the same temperature for 0.5 hours. The reaction mixture was heated to 60° C., after which the aqueous layer was removed by phase separation. The organic layer was washed with 70 g of 1N HCl and then washed twice with 70 g of water, after which the organic layer was concentrated and brought into dryness, which afforded 11.1 g of a yellowish brown solid. This solid was analyzed by high performance liquid chromatography, and it was found that N-methyl-α-methoxyimino-2-(2,5-dimethylphenoxymethyl)phenylacetamide was contained at an amount of 9.42 g (28.9 mmol, the yield on the basis of α-methoxyimino-2-(2,5-dimethylphenoxymethyl)phenylacetic acid was 96.1%, E/Z=92/8).

As an impurity, a by-product formed by condensation of two N-methyl-α-methoxyimino- 2-(2,5-dimethylphenoxymethyl)phenylacetamide molecules through a sulfur molecule was contained at a content of 1.5% (on the basis of α-methoxyimino-2-( 2,5-dimethylphenoxymethyl)phenylacetic acid).

Then, 10.3 g of this solid was recrystallized from toluene to gave 7.22 g of yellowish white crystals. These crystals were analyzed by high performance liquid chromatography, and it was found that the purity of N-methyl-α-methoxyimino-2-(2,5-dimethylphenoxymethyl)phenylacetamide was 97.3% (E/Z=98/2).

Reference Example 1-(4)

A toluene solution containing α-methoxyimino-2-(2,5-dimethylphenoxymethyl)phenylacetyl chloride produced in accordance with Example 6-(4) was added dropwise to a mixture of 100 g of toluene, 24.8 g (320 mmol) of 40% aqueous methylamine solution and 50 g of water at 10°–20° C. over 0.5 hours, and the reaction was allowed to proceed at the same temperature for 0.5 hours. The reaction mixture was heated to 60° C., and the aqueous layer was removed by phase separation. The organic layer was washed with 70 g of 1N HCl and then washed twice with 70 g of water, after which the organic layer was concentrated and brought into dryness, which afforded 10.9 g of a yellowish brown solid.

This solid was analyzed by high performance liquid chromatography, and it was found that N-methyl-α-methoxyimino-2-(2,5-dimethylphenoxymethyl)phenylacetamide was contained at an amount of 8.83 g (27.1 mmol, the yield on the basis of α-methoxyimino- 2-(2,5-dimethylphenoxymethyl)phenylacetic acid was 90.2%, E/Z=93/7).

As an impurity, a by-product formed by condensation of two N-methyl-α-methoxyimino- 2-(2,5-dimethylphenoxymethyl)phenylacetamide molecules through a sulfur molecule was contained at a content of 4.2% (on the basis of α-methoxyimino-2-(2,5-dimethylphenoxymethyl)phenylacetic acid).

Reference Example 1-(5)

First, 58.7 g of a toluene solution containing 8.04 g (24.5 mmol, E/Z=95/5) of methyl α-methoxyimino-2-(2,5-dimethylphenoxymethyl)phenylacetate produced in accordance with Example 7-(2) was concentrated to become 22.0 g, to which 10 ml of methanol was added for dilution and 31.3 g (302 mmol) of a methanol solution of 30% methylamine was added dropwise at 20°–25° C. over 1 hour, and the reaction was subsequently allowed to proceed at the same temperature for 10 hours. After the reaction, the reaction mixture was concentrated and dried, which afforded 8.91 g of a yellowish brown solid.

This solid was analyzed by high performance liquid chromatography, and it was found that N-methyl-α-methoxyimino-2-(2,5-dimethylphenoxymethyl)phenylacetamide was contained at an amount of 7.64 g (23.4 mmol, 95.5% yield, E/Z=94/6).

Then, 8.55 g of this solid was recrystallized from toluene to give 6.44 g of yellowish white crystals. These crystals were analyzed by high performance liquid chromatography, and it was found that the purity of N-methyl-α-methoxyimino-2-(2,5-dimethylphenoxymethyl)phenylacetamide was 97.4% (E/Z=99/1).

Reference Example 1-(6)

To a mixture of 67.13 g of water, 41.38 g (533 mmol) of 40% aqueous methylamine solution and 120 g of toluene were simultaneously added dropwise 589.4 g of a toluene solution containing α-methoxyimino-2-(2,5-dimethylphenoxymethyl)phenylacetyl chloride obtained in accordance with Example 6-(1) and 77.23 g (444 mmol) of 23% aqueous sodium hydroxide solution at 20°–25° C. over 6 hours while adjusting the pH to 10 or higher, and the reaction was subsequently allowed to proceed at the same temperature for 1 hour. The reaction mixture was heated to 65° C., and the aqueous layer was removed by phase separation. The organic layer was washed with 170 g of 1N HCl and then washed twice with 170 g of water which afforded 700.6 g of a toluene solution containing N-methyl-α-methoxyimino-2-(2,5-dimethylphenoxymethyl)phenylacetamide.

This solution was analyzed by high performance liquid chromatography, and it was found that the content of N-methyl-α-methoxyimino-2-(2,5-dimethylphenoxymethyl)phenylacetamide was 20.1% and the yield on the basis of the starting α-methoxyimino- 2-(2,5-dimethylphenoxymethyl)phenylacetic acid was 96.9% (E/Z=93/7).

Reference Example 1-(7) Production of N-alkyl-α-alkoxyiminophenylacetamide [IX]

To a mixture of 60.8 g (0.782 mol) of 40% aqueous methylamine solution and 44 g of toluene was added dropwise 265 g of a toluene solution containing α-methoxyimino- 2-(4-chloro-2-methylphenoxymethyl)phenylacetyl chloride obtained in Example 6-(5) at 10°–15° C. over 2 hours, and the reaction was subsequently allowed to proceed at the same temperature for 0.5 hours. The reaction mixture was heated to 65° C., and the aqueous layer was removed by phase separation. The organic layer was washed twice with 75 g of 1N HCl, which afforded 306 g of a toluene solution containing N-methyl-α-methoxyimino- 2-(4-chloro-2-methylphenoxymethyl)phenylacetamide.

Reference Example 2-(1) E/Z Isomerization

First, 1143 g of a toluene solution containing 228.4 g (700 mmol, E/Z= 93.6/6.4) of N-methyl-α-methoxyimino-2-(2,5-dimethylphenoxymethyl)phenylacetamide obtained in accordance with Reference Example 1-(6) was heated to 60°–65° C., to which 70.85 g (700 mmol) of 36% hydrochloric acid was added dropwise over 1 hour, and the stirring was continued at the same temperature for 2 hours. While maintaining the same temperature, 233 g of water was added to the reaction mixture, and the aqueous layer was removed by phase separation. Further, the organic layer was washed twice with 280 g of water. The organic layer was concentrated and brought into dryness, which afforded 258.9 g of a brown solid. This solid was analyzed by high performance liquid chromatography, and it was found that the content of N-methyl-α-methoxyimino-2-(2,5-dimethylphenoxymethyl)phenylacetamide was 88.1% (E/Z=95.2/4.8, 99.9% recovery).

Then, 22.91 g of the above brown solid was dissolved in toluene and recrystallized to give 17.59 g of yellowish white crystals. The analysis by high performance liquid chromatography revealed that the purity of N-methyl-α-methoxyimino-2-( 2,5-dimethylphenoxymethyl)phenylacetamide was 99.6% (E/Z=99.0/1.0).

The filtrate (toluene solution) after the recrystallization, containing 11.51 g (35.3 mmol, E/Z=66.4/33.6) of N-methyl-α-methoxyimino-2-(2,5-dimethylphenoxymethyl)phenylacetamide obtained in accordance with the above recrystallization was concentrated to become 67.08 g, to which 4.00 g (39.5 mmol) of 36% HCl was added, and the reaction was allowed to proceed at 65°–70° C. for 3 hours. The reaction mixture was washed three times with 15 g of water, and the organic layer was concentrated to become 42.44 g and cooled to cause the precipitation of crystals. The precipitated crystals were filtered, washed with a slight amount of toluene and dried, which afforded 8.93 g of yellowish brown crystals. The analysis by high performance liquid chromatography revealed that the content of N-methyl-α-methoxyimino-2-(2,5-dimethylphenoxymethyl)phenylacetamide was 88.2% (E/Z=99.0/1.0).

Then, 7.70 g of these crystals were dissolved in toluene and recrystallized to give 5.74 g of yellowish white crystals. The analysis by high performance liquid chromatography revealed that the purity of N-methyl-α-methoxyimino-2-(2,5-dimethylphenoxymethyl)phenylacetamide was 98.8% (E/Z=99.9/0.1).

Reference Example 2-(2) E/Z Isomerization

First, 306 g of a toluene solution containing N-methyl-α-methoxyimino-2-(4-chloro- 2-methylphenoxymethyl)phenylacetamide obtained in accordance with Reference Example 1-(7) was heated to 60°–65° C., to which 22.2 g (219 mmol) of 36% hydrochloric acid was added dropwise over 1 hour, and the stirring was continued at the same temperature for 3 hour. While keeping the same temperature, 60 g of water was added to the reaction mixture, and the aqueous layer was removed by phase separation. Further, the organic layer was washed twice with 75 g of water. The organic layer was concentrated and brought into dryness, which afforded 53.77 g of pale brown crystals. These crystals were analyzed by high performance liquid chromatography, and it was found that the content of N-methyl-α-methoxyimino-2-(4-chloro-2-methylphenoxymethyl)phenylacetamide was 98.4% (E/Z=95.6/4.4) and the yield on the basis of N-methyl-α-methoxyimino- 2-(4-chloro-2-methylphenoxymethyl)phenylacetonitrile was 96.6%.

Industrial Utilization

According to the present invention, the reactions can be allowed to proceed under mild conditions over the whole process, and the desired carboxylic acid derivative [VIII] can be produced without any facilities such as high-pressure steam equipment, high-temperature heat medium control equipment and freezing machines. In addition, there is no need to use various different solvents in the respective steps and the present process can be conducted with only one solvent, in which respect the present invention is also advantageous.

We claim:

1. A process for producing a carboxylic acid derivative of the general formula [VIII]:

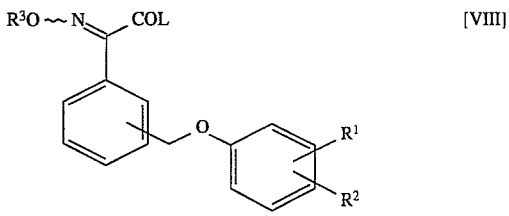

wherein $R^1$, $R^2$ and $R^3$ are each as defined below and L is halogen or $C_1$-$C_5$ alkoxy, characterized in that:

a benzyl halide of the general formula [III]:

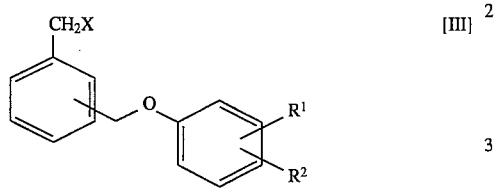

wherein $R^1$ and $R^2$ are the same or different and are independently hydrogen, $C_1$-$C_5$ alkyl, $C_1$-$C_5$ alkoxy, $C_2$-$C_4$ alkenyl, halogen or trifluoromethyl, and X is halogen, is reacted with a cyano compound to give a phenylacetonitrile of the general formula [IV]:

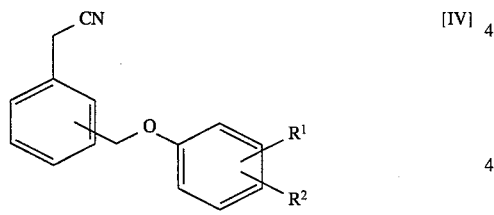

wherein $R^1$ and $R^2$ are each as defined above;

this compound is reacted with an alkyl nitrite in the presence of a base to give an α-hydroxyiminophenylacetonitrile of the general formula [V]:

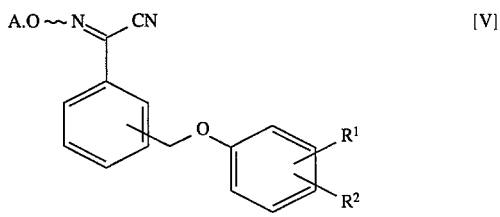

wherein $R^1$ and $R^2$ are each as defined above and A is an alkali metal or an alkaline earth metal;

this compound is reacted with an alkylating agent to give an α-alkoxyiminophenylacetonitrile of the general formula [VI]:

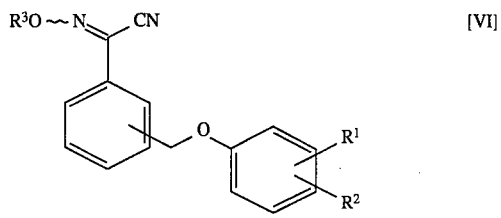

wherein $R^1$ and $R^2$ are each as defined above and $R^3$ is $C_1$-$C_5$ alkyl;

this compound is hydrolyzed in the presence of a base, or this compound is hydrated and treated with an acid, followed by hydrolysis in the presence of a base, to give an α-alkoxyiminophenylacetic acid of the general formula [VII]

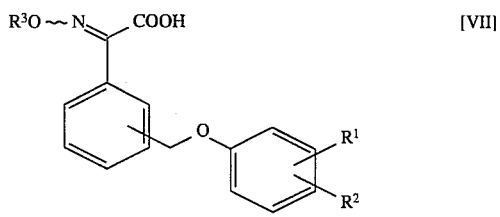

wherein $R^1$, $R^2$ and $R^3$ are each as defined above; and this compound is reacted with an acid halide forming agent, or converted into a metal salt and then reacted with an alkylating agent, or reacted with a lower alcohol in the presence of an acid catalyst.

2. A production process according to claim 1, wherein the benzyl halide of the general formula [III] is produced by reacting a metal salt of a phenol derivative of the general formula [I]:

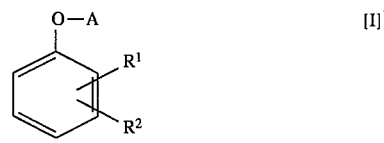

wherein $R^1$, $R^2$ and A are each as defined above, with an α,α'-dihaloxylene derivative of the general formula [II]:

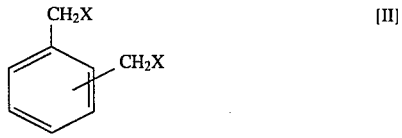

wherein X is as defined above.

3. A production process according to claim 1, wherein a hydrocarbon solvent or a mixed solvent containing a hydrocarbon solvent is used as a solvent.

4. A production process according to claim 3, wherein the hydrocarbon solvent is an aromatic solvent.

5. A production process according to claim 4, wherein the aromatic solvent is toluene.

6. A production process according to claim 1, wherein the α-hydroxyiminophenylacetonitrile [V] is produced by reacting the phenylacetonitrile [IV] with an alkyl nitrite in the presence of a base; extracting the reaction mixture with water; and neutralizing the separated aqueous layer with an acid.

7. A production process according to claim 1, wherein the α-alkoxyiminophenylacetonitrile [VI] is produced by reacting the α-hydroxyiminophenylacetonitrile [V] with an alkylating agent in the presence of a phase transfer catalyst in a mixed solvent system consisting of a hydrocarbon solvent and water.

8. A production process according to claim 2, wherein the benzyl halide [III] is produced by reacting the α,α'-dihaloxylene derivative [II] at a ratio of not less than 1.5 times the moles of the metal salt of the phenol derivative [I].

9. A production process according to claim 2, wherein the α,α'-dihaloxylene derivative [II] is reacted at a ratio of 2 to 6 times the moles of the metal salt of the phenol derivative [I] to give the benzyl halide [III].

10. A production process according to claim 1, wherein the $R^1$ and $R^2$ are hydrogen, halogen or $C_1$-$C_5$ alkyl.

11. A production process according to claim I, wherein the $R^1$ and $R^2$ are hydrogen, chlorine or methyl.

12. A production process according to claim 1, wherein the α-alkoxyiminophenylacetic acid [VII] is converted into a metal salt which is then reacted with an alkylating agent, followed by treatment with an acid; or the α-alkoxyiminophenylacetic acid [VII] is reacted with a lower alcohol in the presence of an acid catalyst, followed by treatment with an acid.

* * * * *